(12) United States Patent
Kumano et al.

(10) Patent No.: US 11,371,915 B2
(45) Date of Patent: Jun. 28, 2022

(54) ADHERING SUBSTANCE COLLECTING DEVICE AND INSPECTION SYSTEM

(71) Applicant: Hitachi, Ltd., Tokyo (JP)

(72) Inventors: Shun Kumano, Tokyo (JP); Masuyuki Sugiyama, Tokyo (JP); Hisashi Nagano, Tokyo (JP); Makoto Namai, Tokyo (JP); Takahiro Itou, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 780 days.

(21) Appl. No.: 16/305,812

(22) PCT Filed: May 29, 2017

(86) PCT No.: PCT/JP2017/019951
§ 371 (c)(1),
(2) Date: Nov. 29, 2018

(87) PCT Pub. No.: WO2017/209065
PCT Pub. Date: Dec. 7, 2017

(65) Prior Publication Data
US 2020/0319061 A1    Oct. 8, 2020

(30) Foreign Application Priority Data
May 30, 2016   (JP) .............................. JP2016-107972

(51) Int. Cl.
*G01N 1/22*         (2006.01)
*G01N 21/3504*      (2014.01)
(Continued)

(52) U.S. Cl.
CPC ........... *G01N 1/22* (2013.01); *G01N 21/3504* (2013.01); *G01N 33/0057* (2013.01); *G01N 2001/028* (2013.01)

(58) Field of Classification Search
CPC .............................. G01N 1/22; G01N 1/2214
See application file for complete search history.

(56) References Cited

U.S. PATENT DOCUMENTS 5,854,431 A * 12/1998 Linker ..................... G01N 1/40
                                                            73/863.23
2009/0084410 A1   4/2009 Roach et al.
(Continued)

FOREIGN PATENT DOCUMENTS

JP         2014-59268 A     4/2014
WO    WO-2007045862 A1 *   4/2007 ......... G01N 33/0001
(Continued)

OTHER PUBLICATIONS

International Search Report (PCT/ISA/210) issued in PCT Application No. PCT/JP2017/019951 dated Aug. 8, 2017 with English translation (five (5) pages).
(Continued)

*Primary Examiner* — Lisa M Caputo
*Assistant Examiner* — Alex T Devito
(74) *Attorney, Agent, or Firm* — Crowell & Moring LLP

(57) ABSTRACT

In order to detach substances stably from an inspection object, an adhering substance collecting device includes: ejection openings configured to eject gas; a housing on which the ejection openings are provided; and supporting portions which are installed on a surface of the housing on which the ejection openings are provided, and have a prescribed height. The supporting portions include protruded portions formed on the housing. The supporting portions each have a cuboid shape, and are installed such that a distance therebetween becomes smaller toward a direction of a recovery opening that is configured to collect substances having been detached from an inspection object, from the gas.

14 Claims, 24 Drawing Sheets

(51) Int. Cl.
*G01N 33/00* (2006.01)
*G01N 1/02* (2006.01)

(56) References Cited

U.S. PATENT DOCUMENTS

| | | | |
|---|---|---|---|
| 2010/0297602 A1* | 11/2010 | Jones, Jr. | ............... G01N 33/00 435/5 |
| 2014/0151543 A1 | 6/2014 | Nagano et al. | |
| 2015/0233796 A1 | 8/2015 | Kashima et al. | |
| 2015/0311053 A1 | 10/2015 | Stott et al. | |

FOREIGN PATENT DOCUMENTS

| WO | WO 2012/063796 A1 | 5/2012 |
|---|---|---|
| WO | WO 2012/162795 A1 | 12/2012 |
| WO | WO 2014/045649 A1 | 3/2014 |
| WO | WO 2016/027320 A1 | 2/2016 |

OTHER PUBLICATIONS

Japanese-language Written Opinion (PCT/ISA/237) issued in PCT Application No. PCT/JP2017/019951 dated Aug. 8, 2017 (five (5) pages).

\* cited by examiner

[FIG. 1]
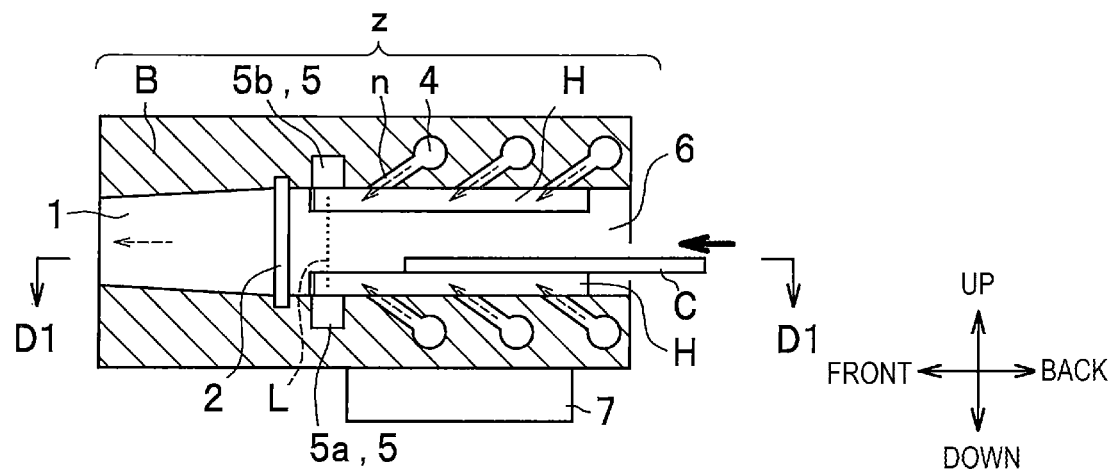
[FIG. 2]
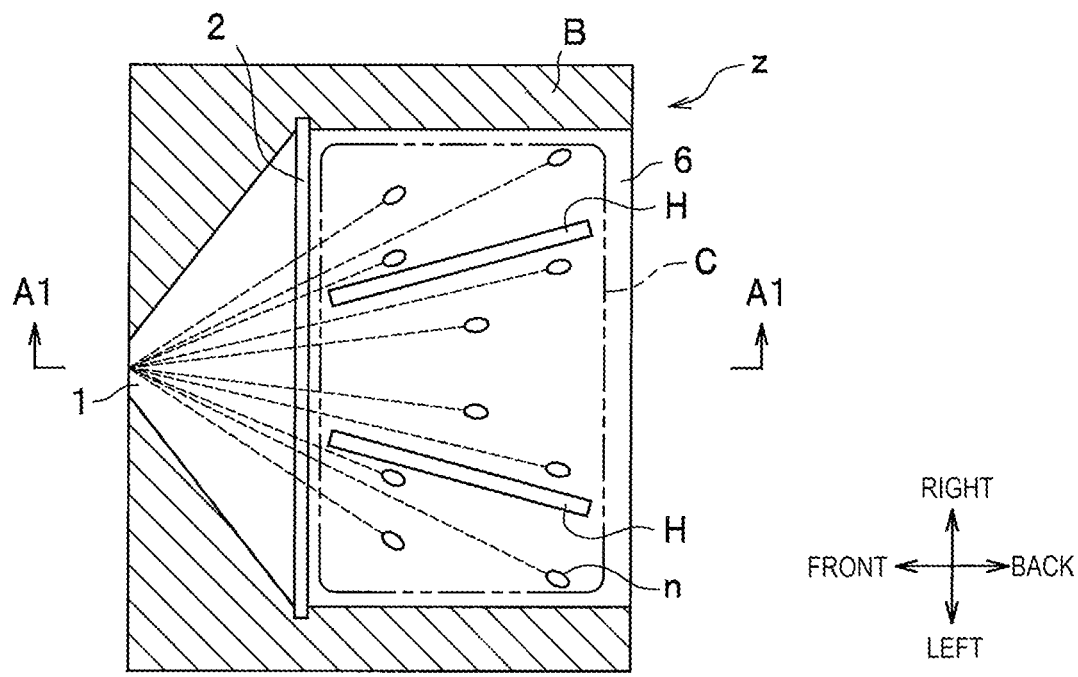

[FIG. 3]
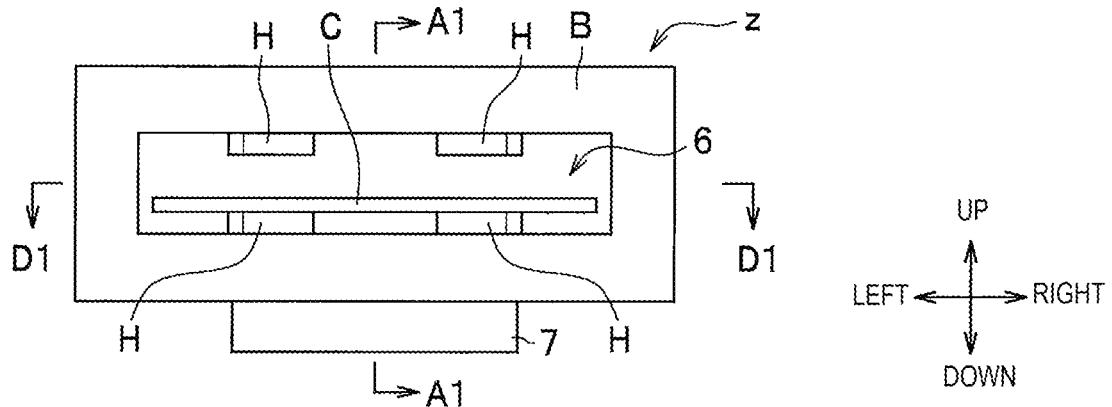
[FIG. 4]
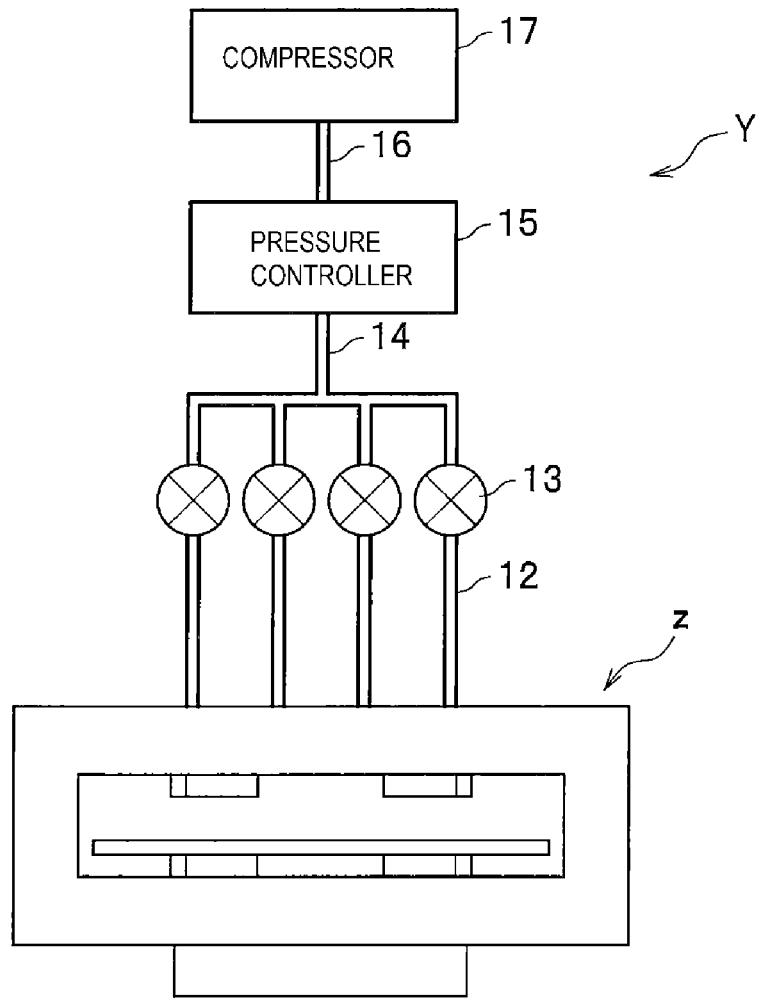

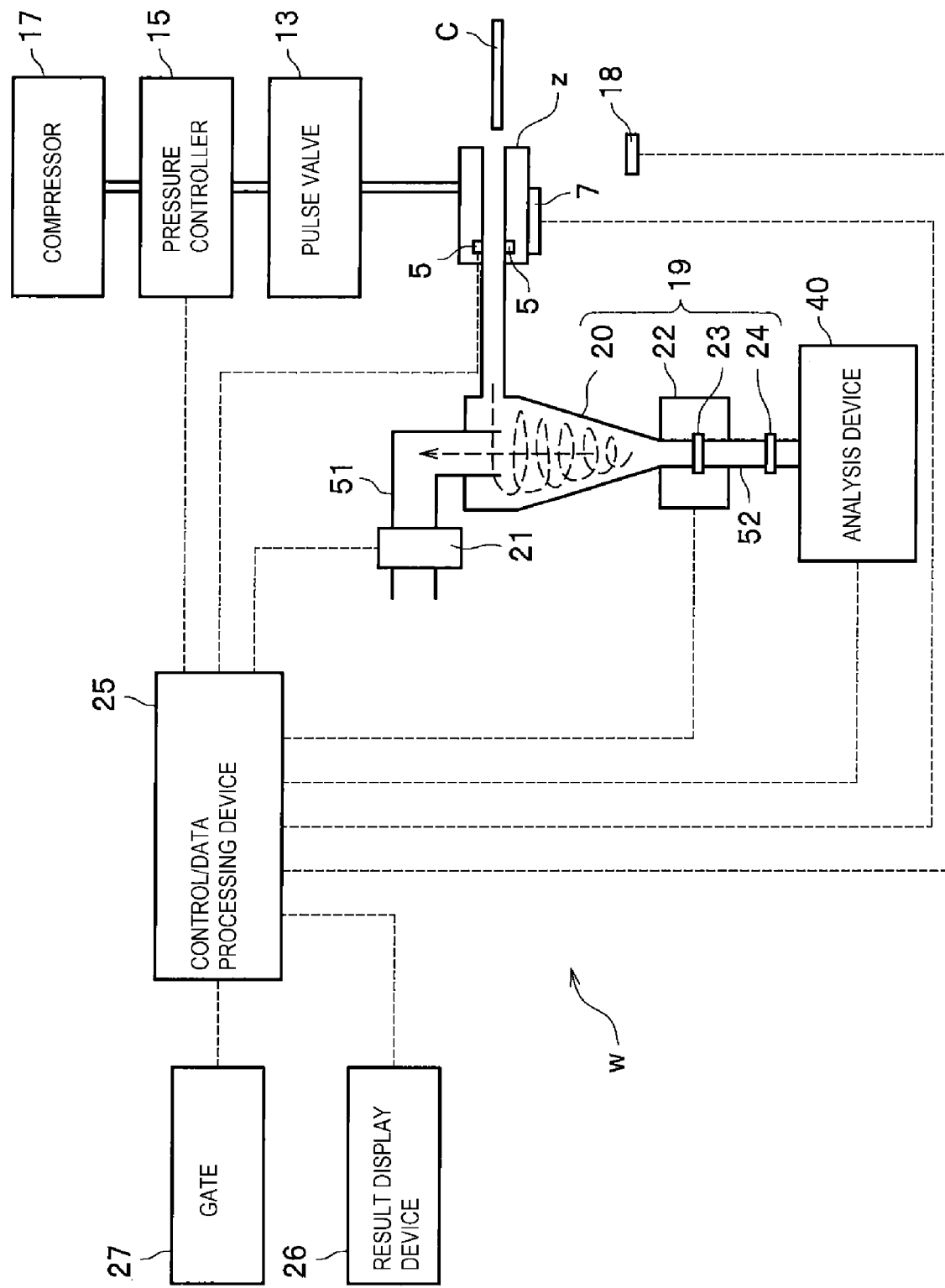
[FIG. 5]

[FIG. 6]
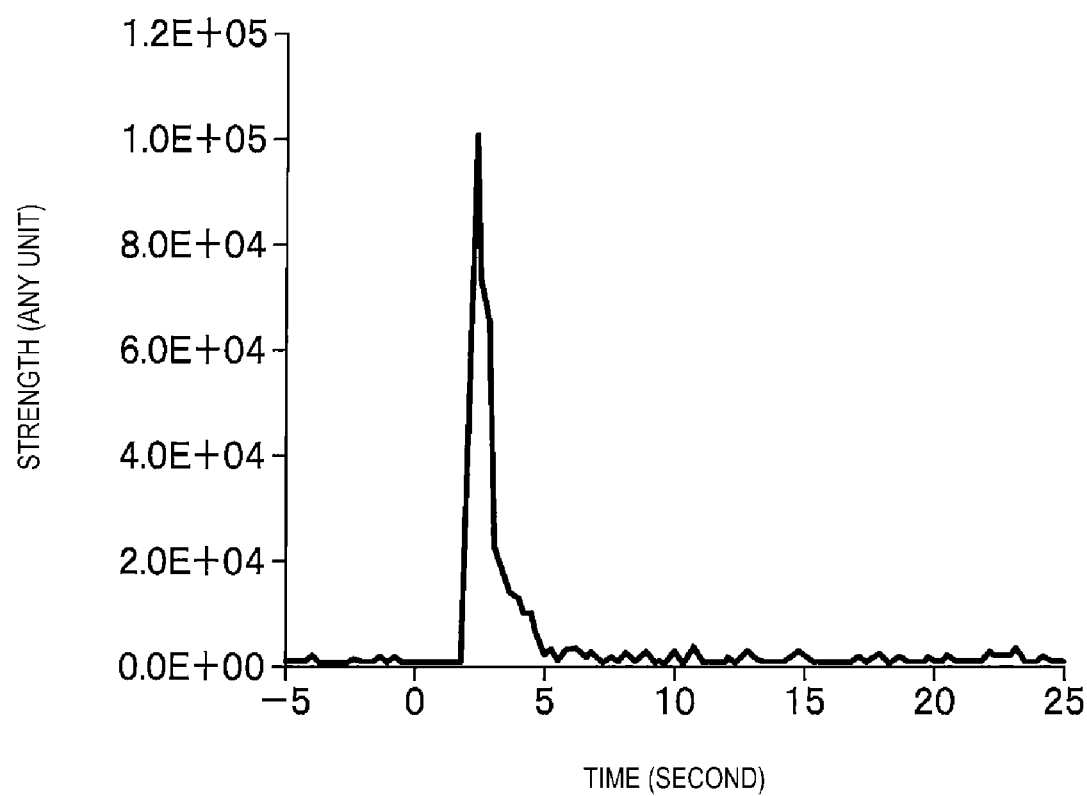

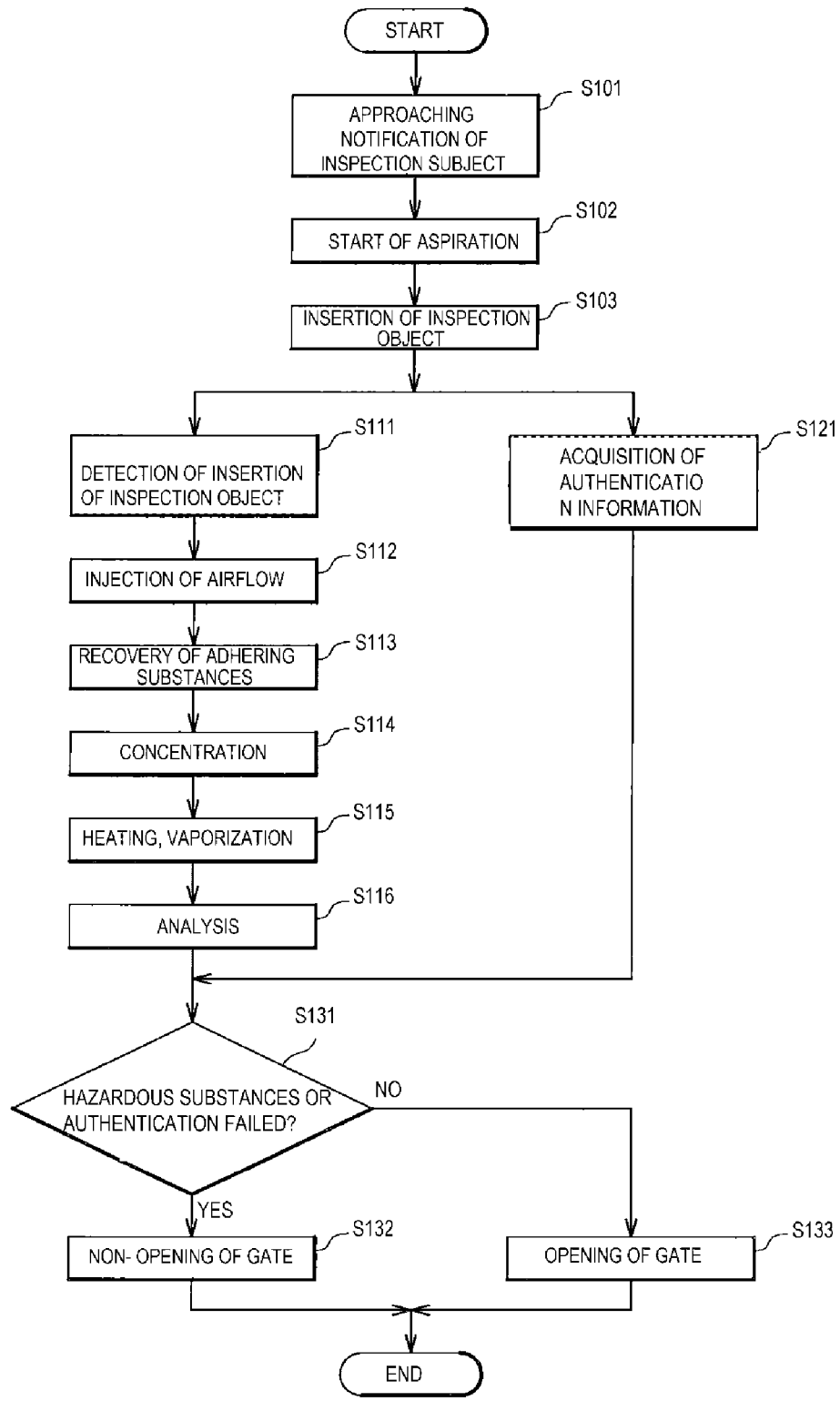
[FIG. 7]

[FIG. 8]
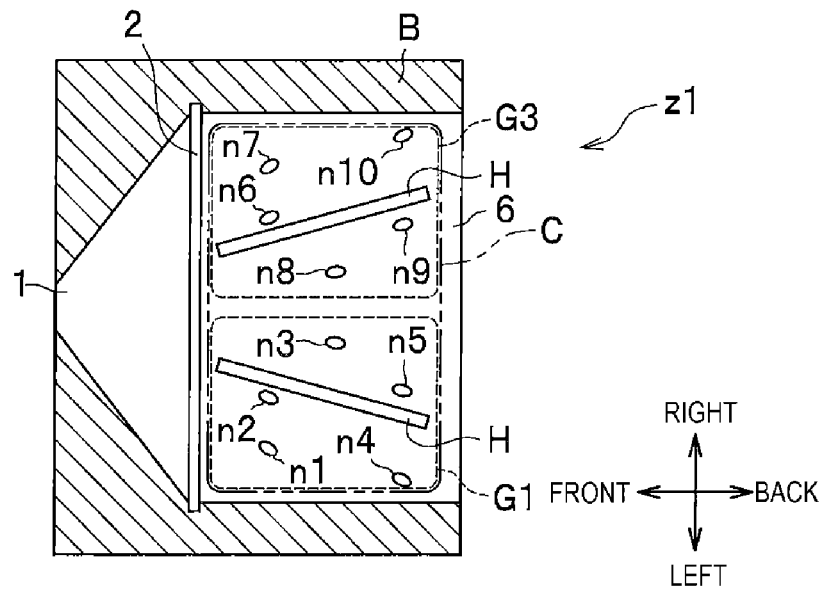
[FIG. 9]
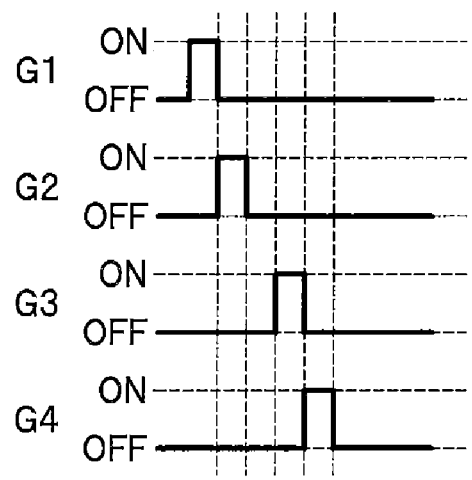

[FIG. 10]
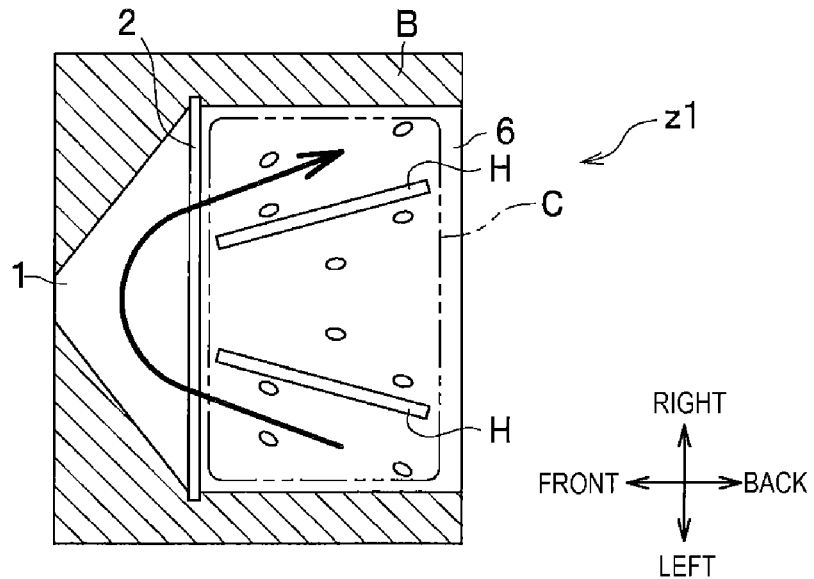
[FIG. 11]
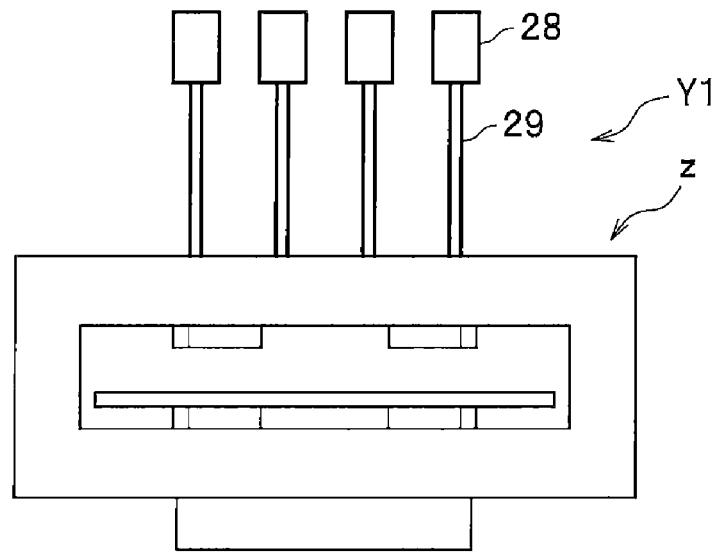

[FIG. 12]
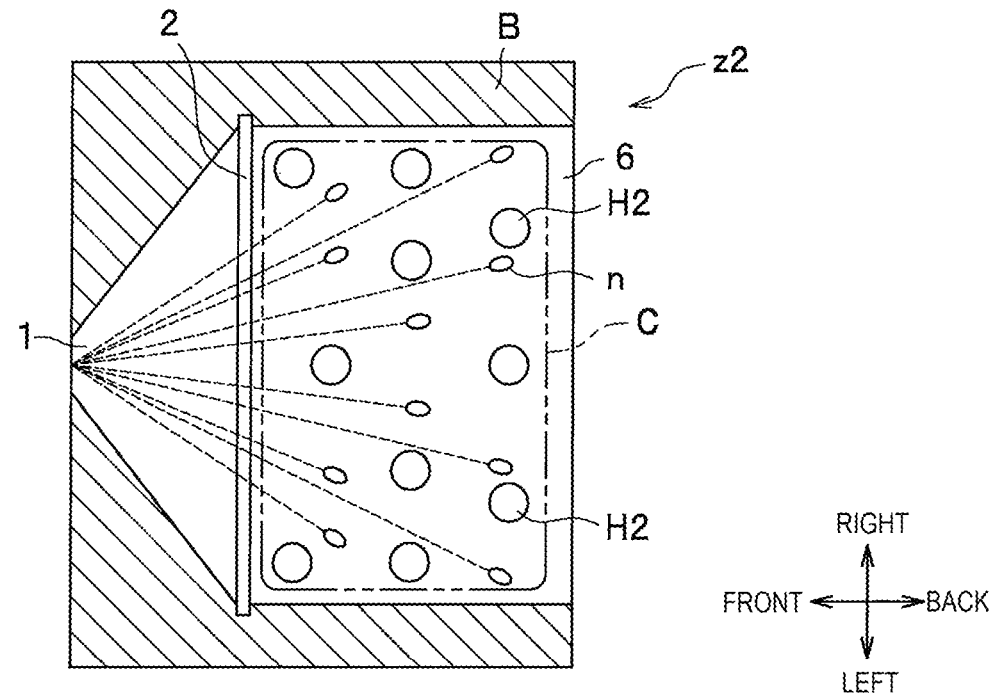
[FIG. 13]
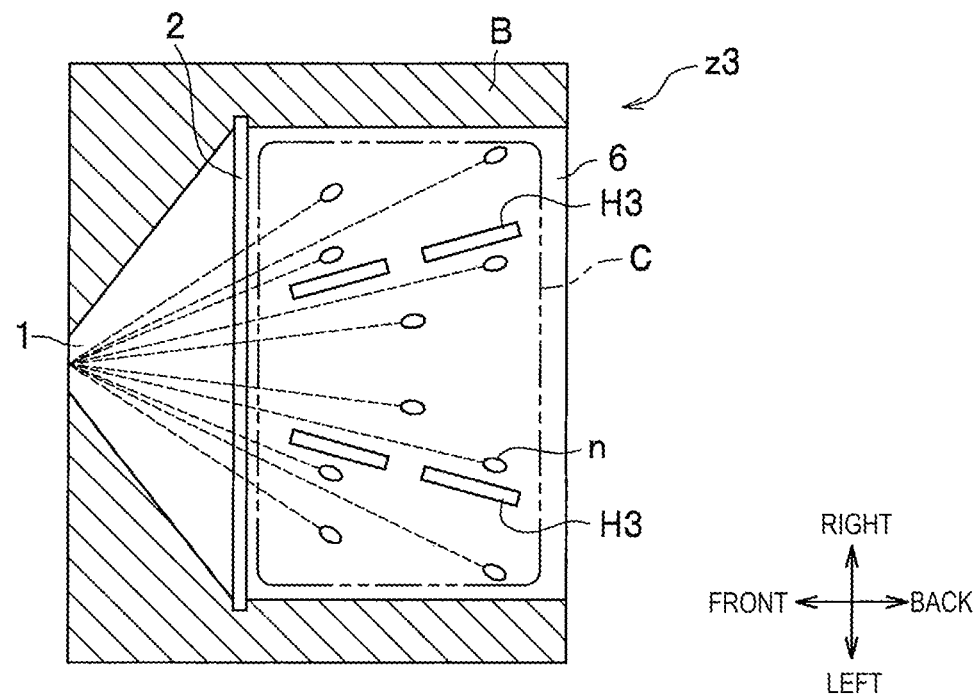

[FIG. 14]
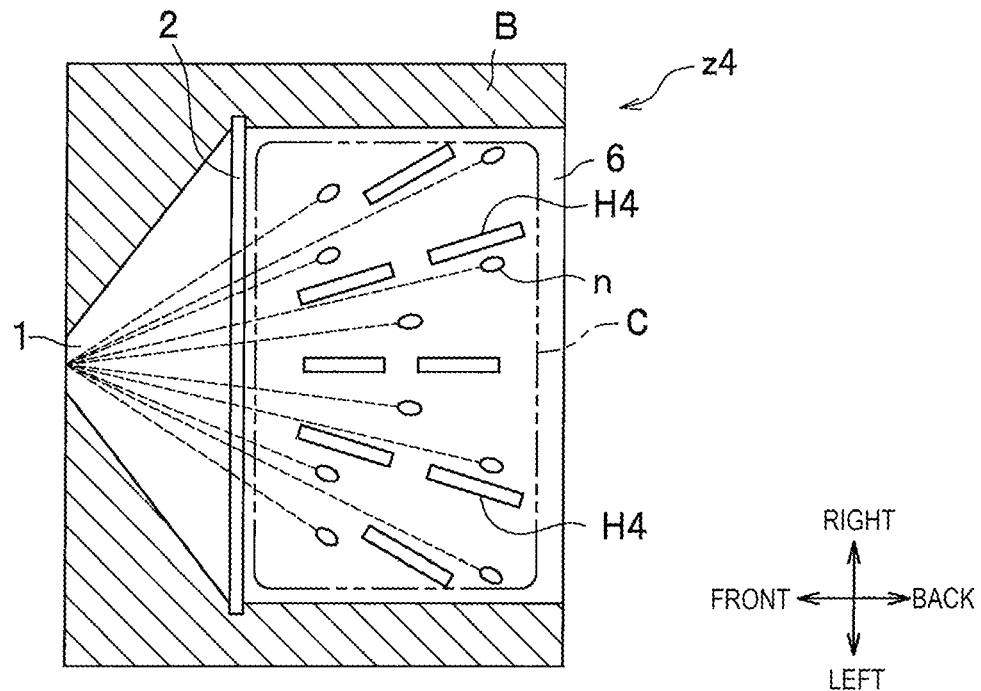
[FIG. 15]
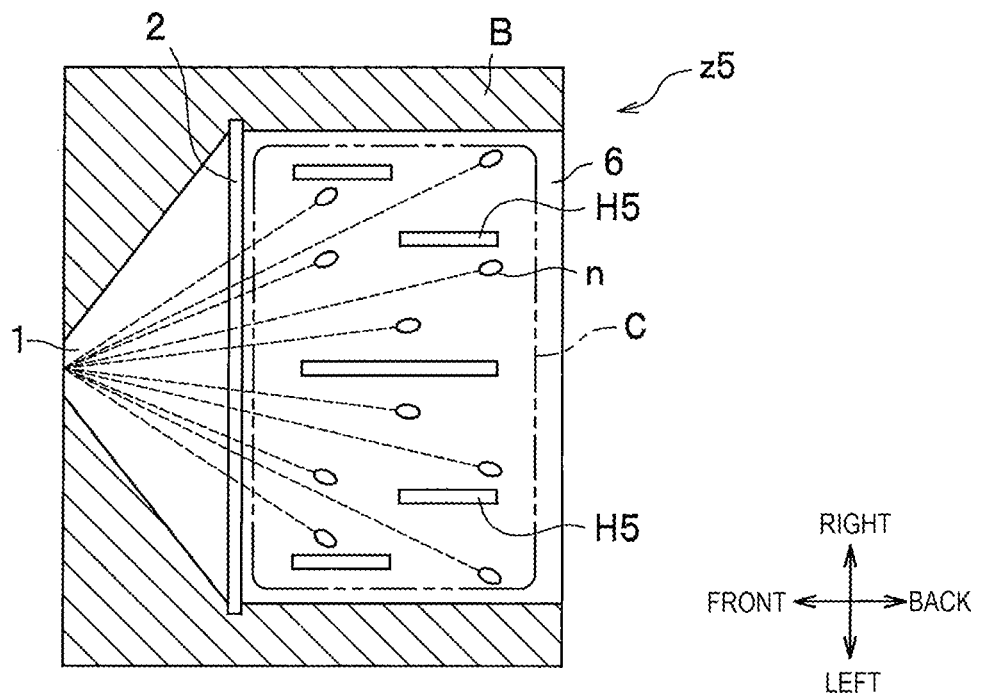

[FIG. 16]
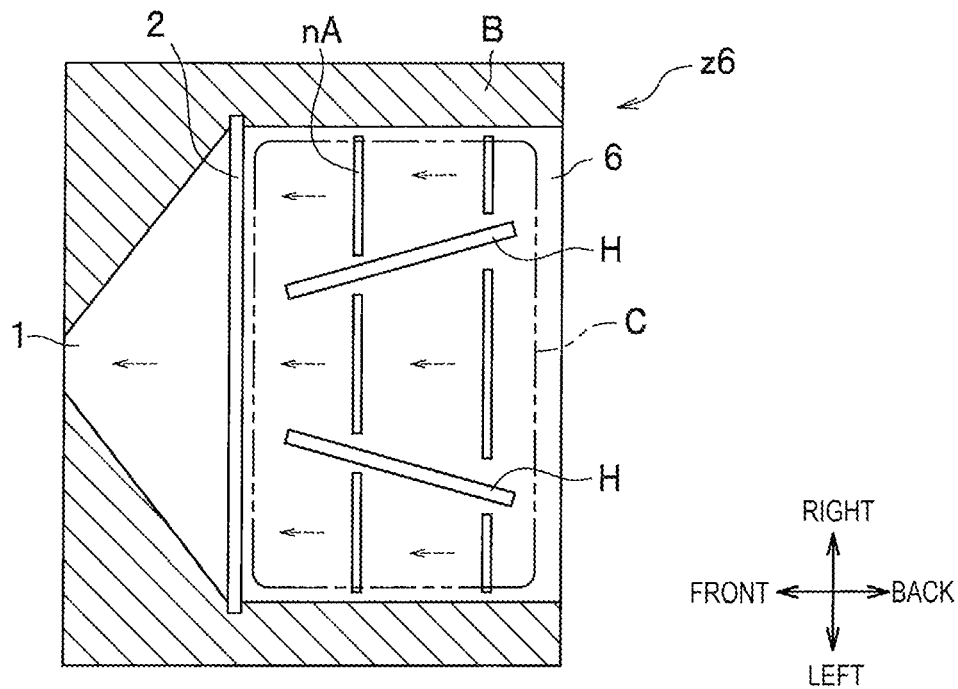
[FIG. 17]
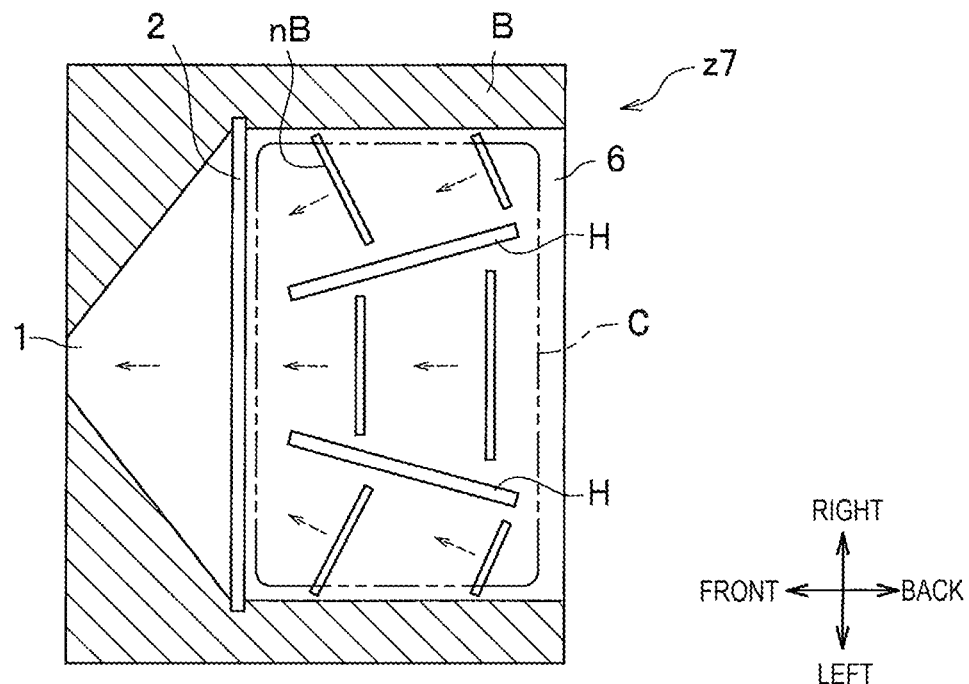

[FIG. 18]
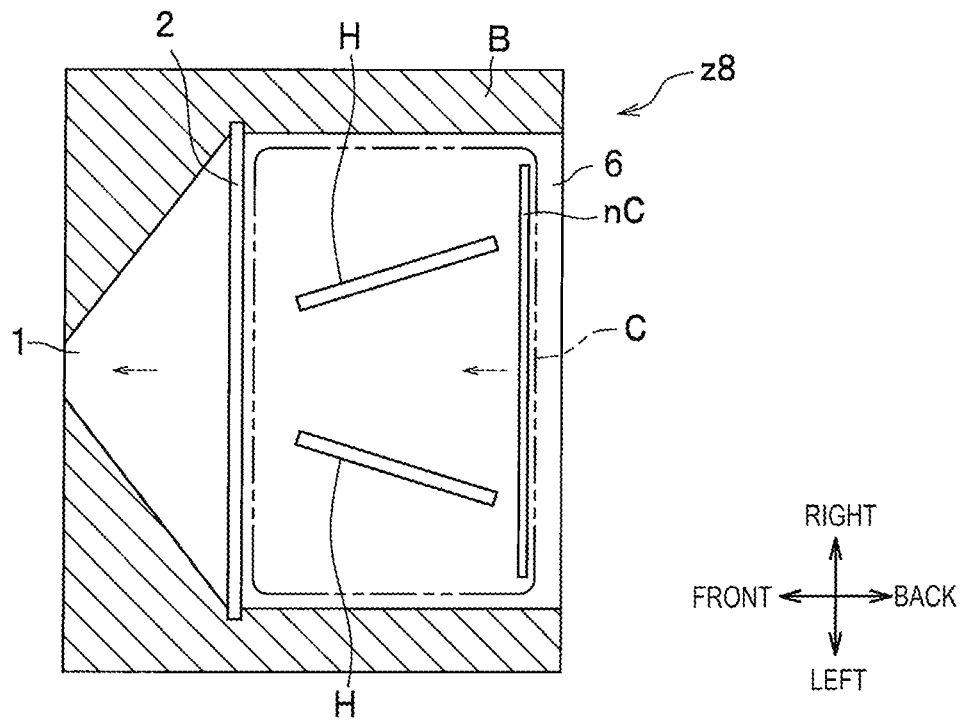
[FIG. 19]
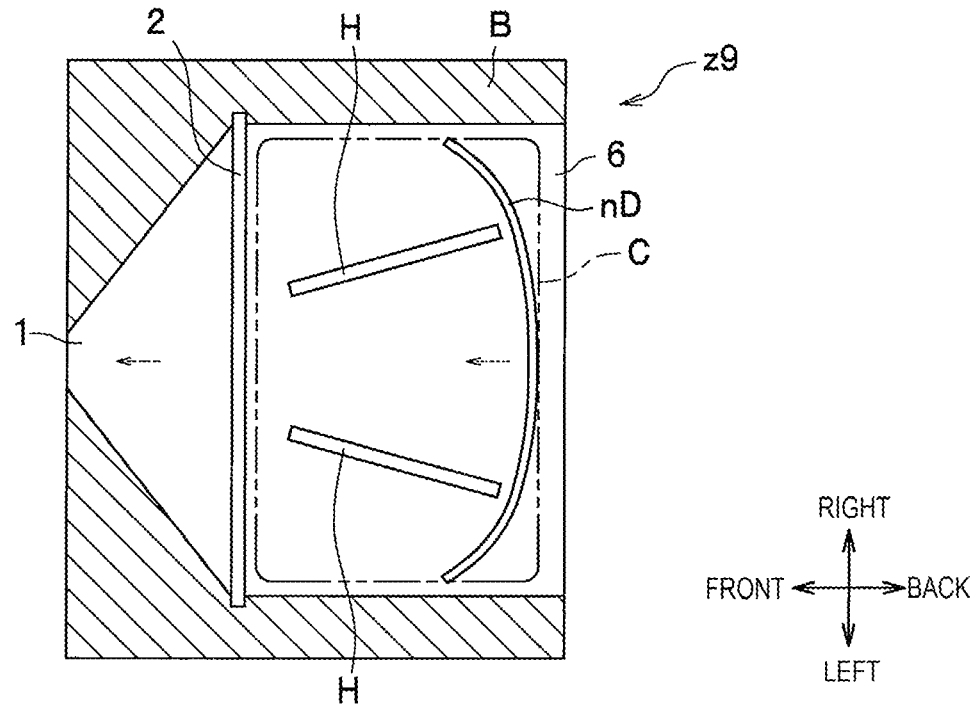

[FIG. 20]
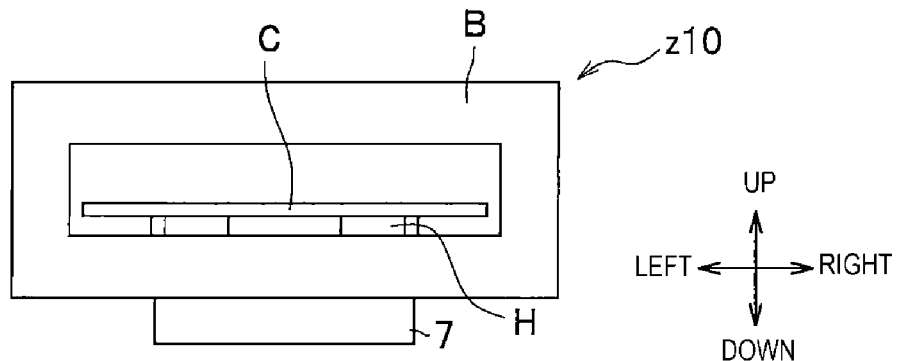
[FIG. 21]
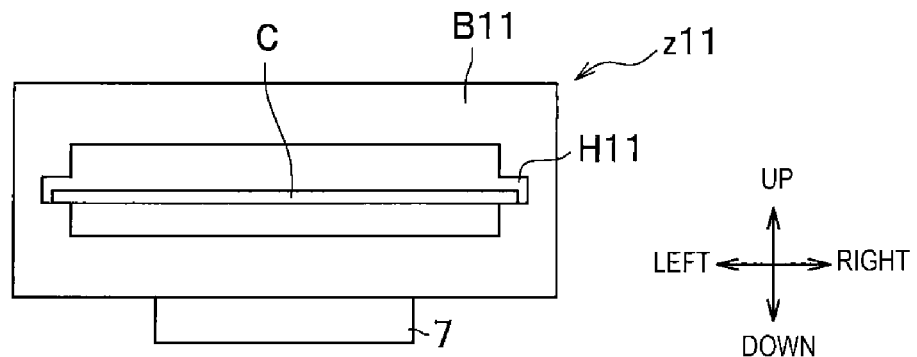
[FIG. 22]
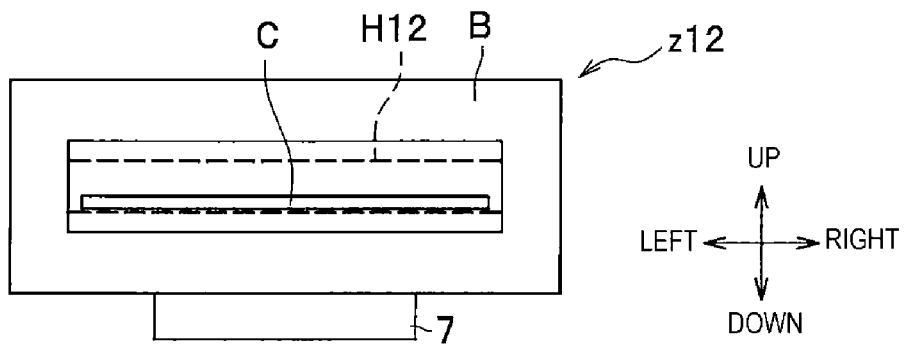

[FIG. 23]
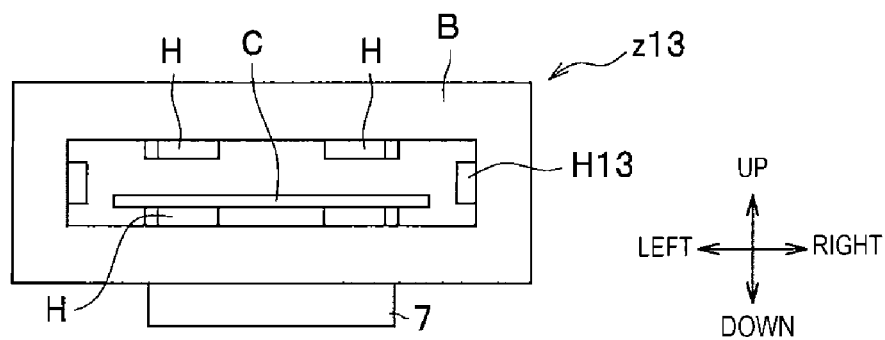
[FIG. 24]
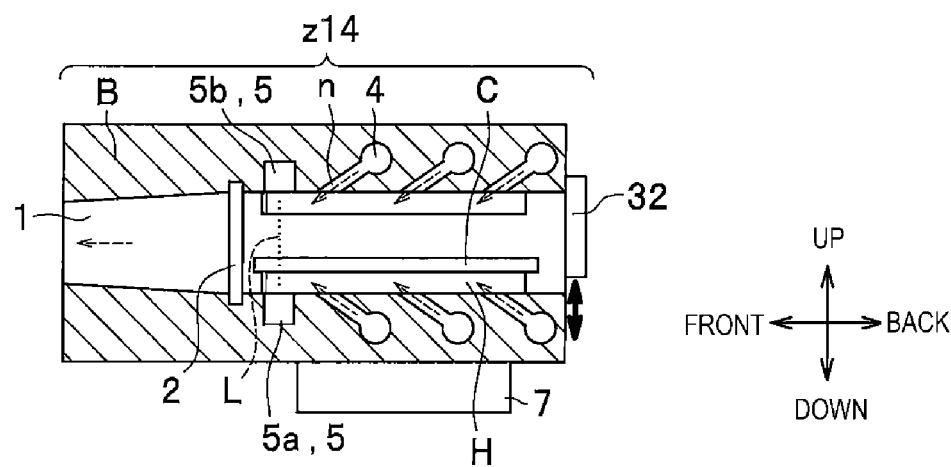

[FIG. 25]
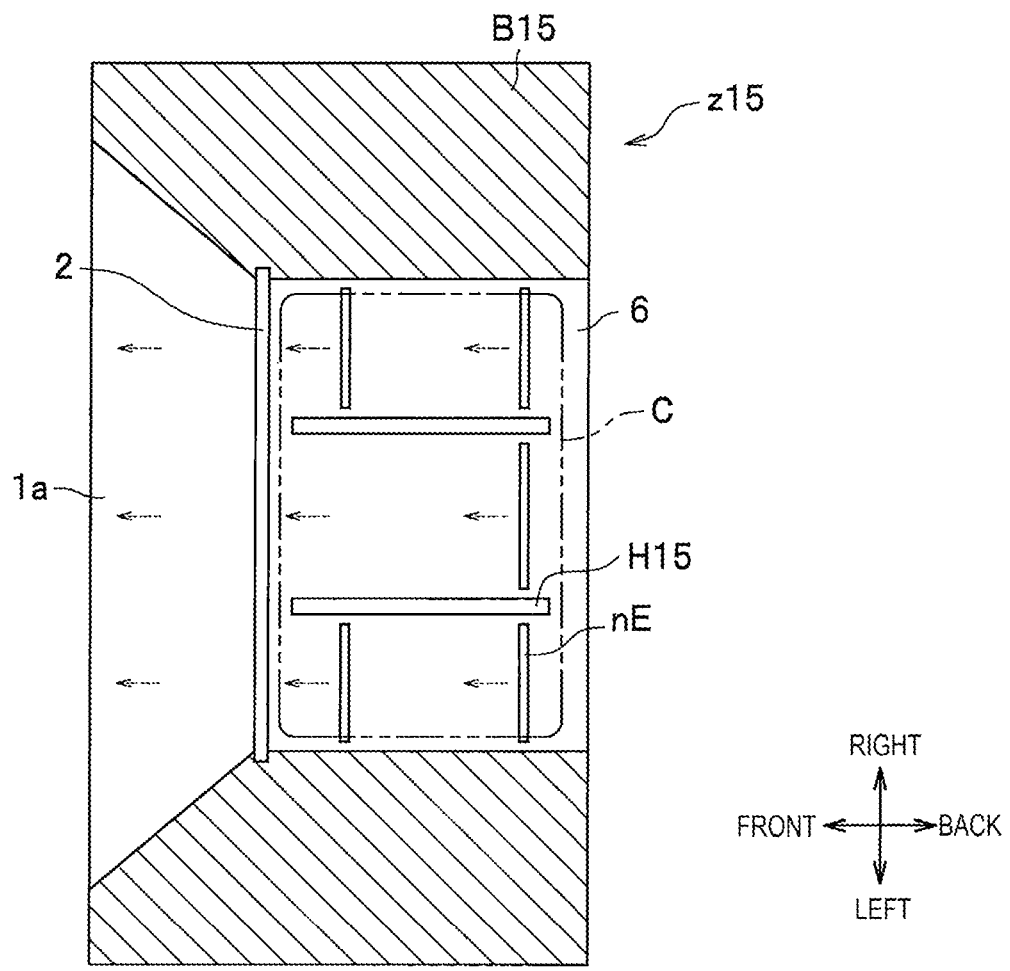

[FIG. 26]
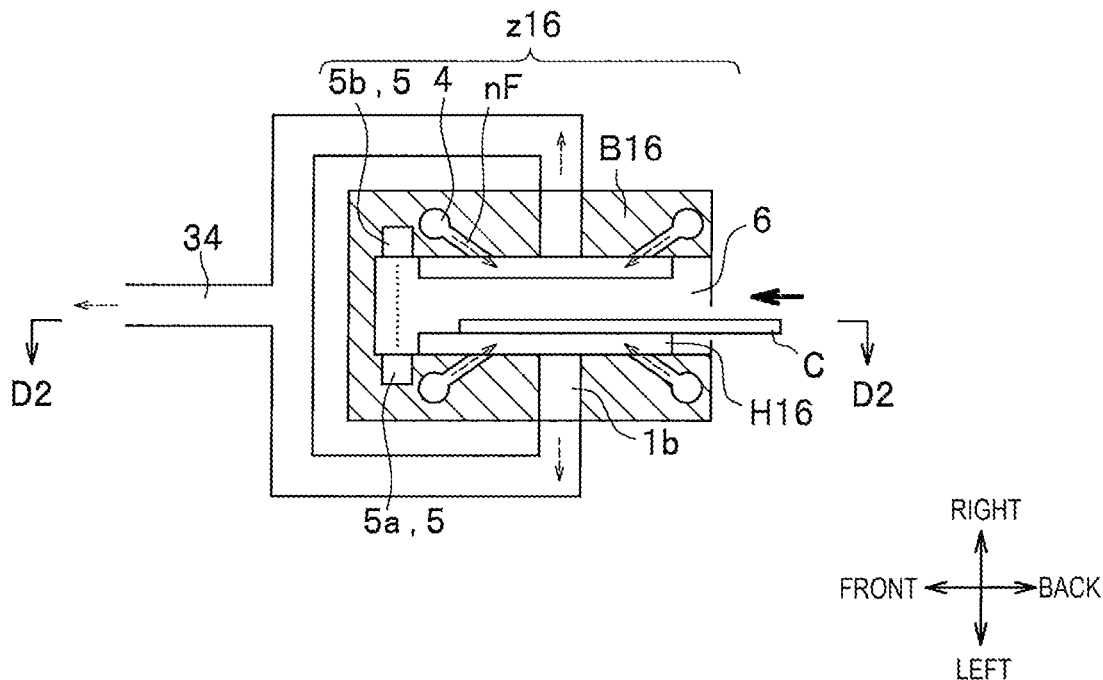
[FIG. 27]
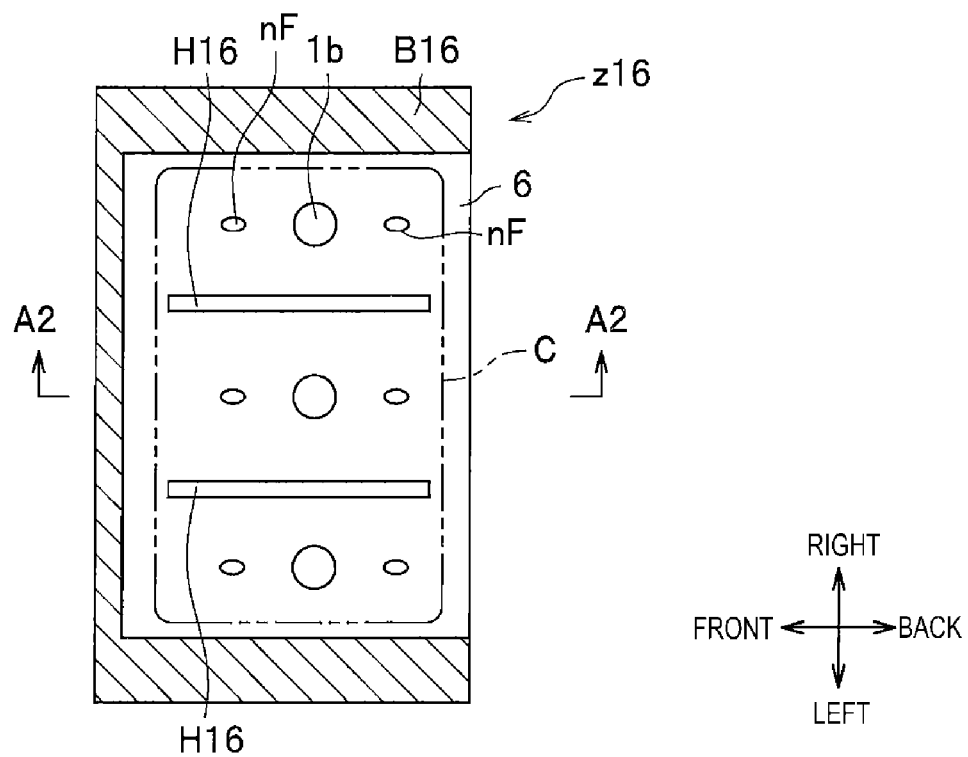

[FIG. 28]
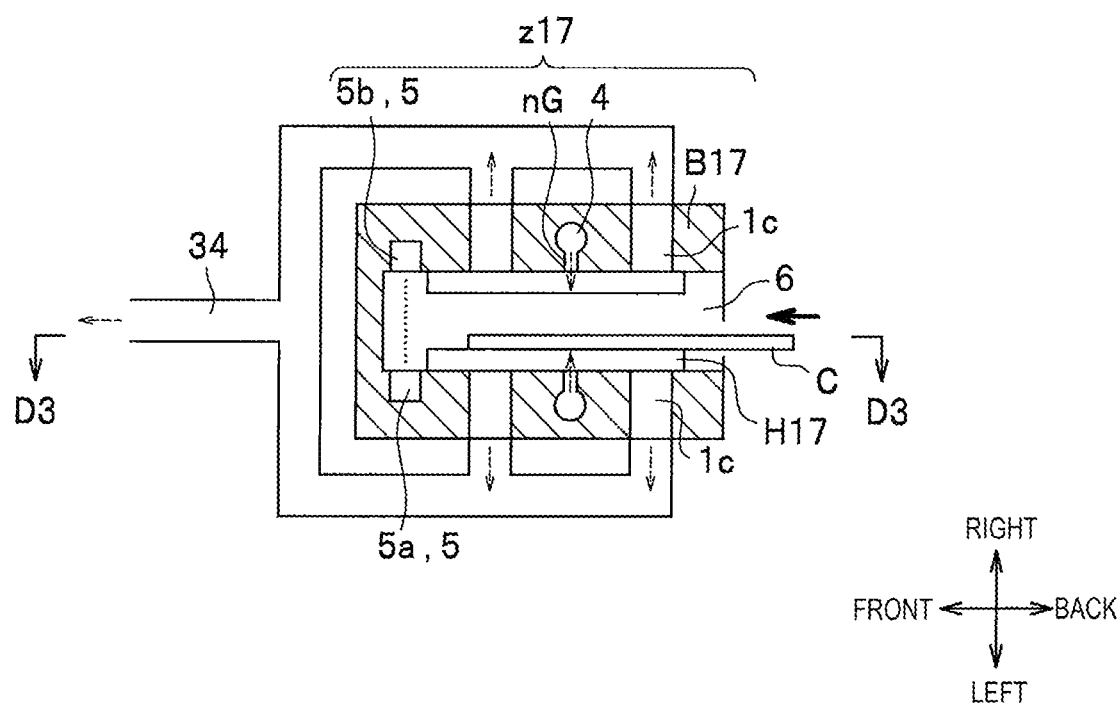

[FIG. 29]
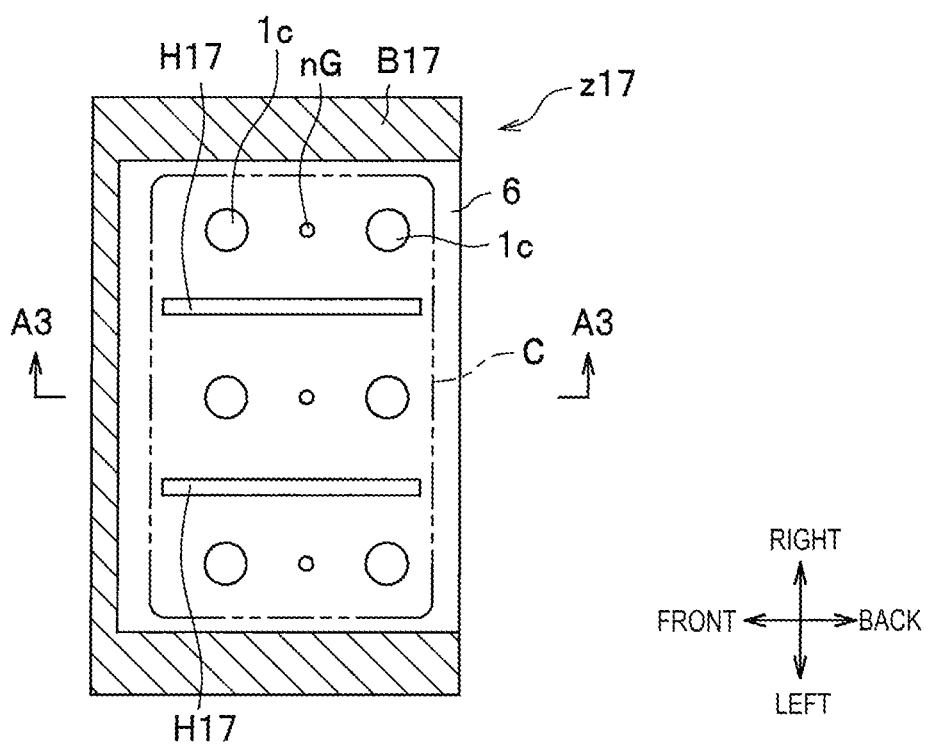

[FIG. 30]
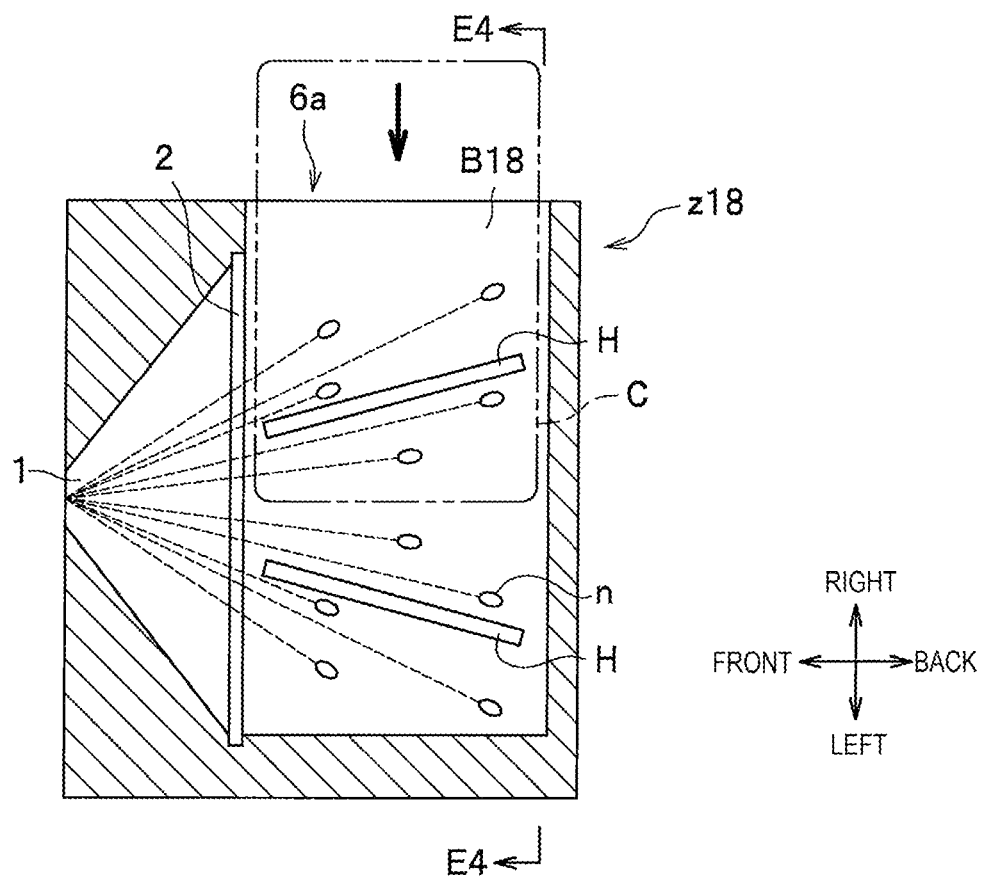
[FIG. 31]
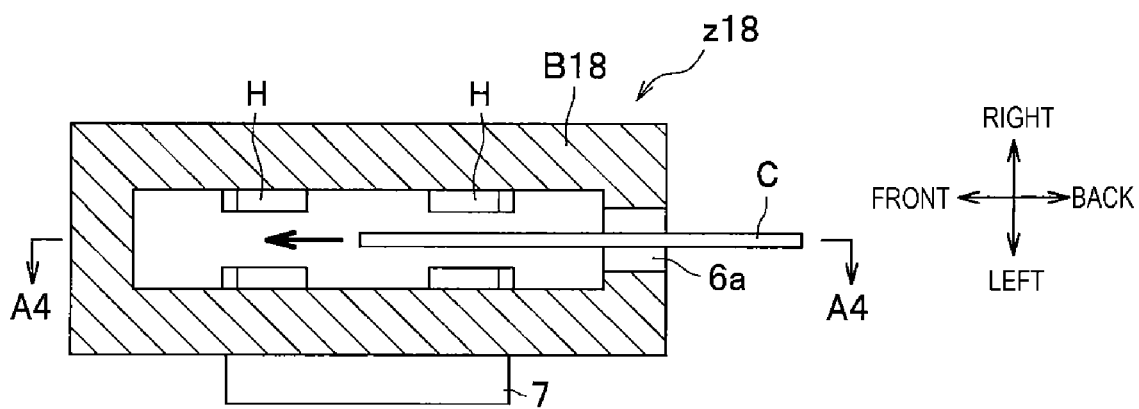

[FIG. 32]
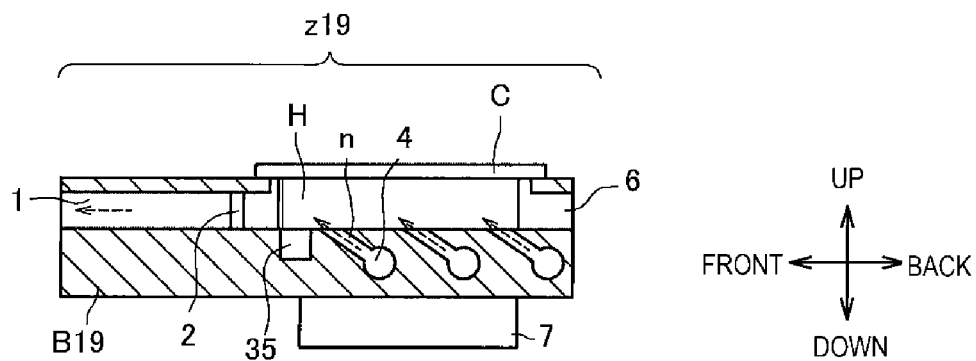
[FIG. 33]
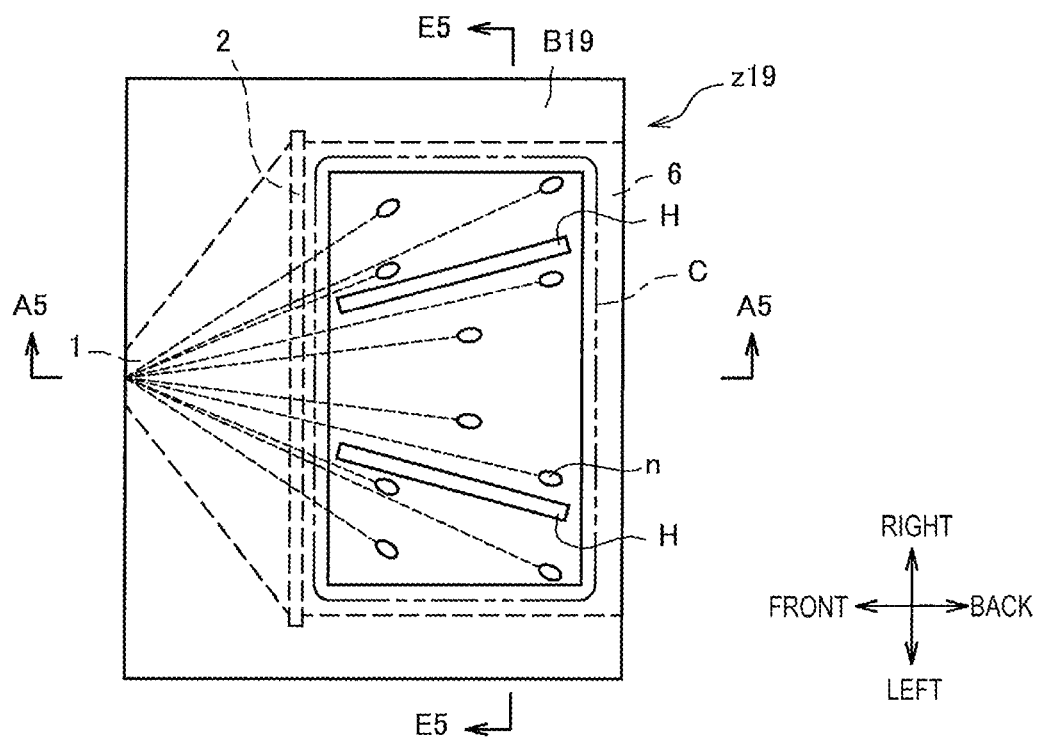

[FIG. 34]
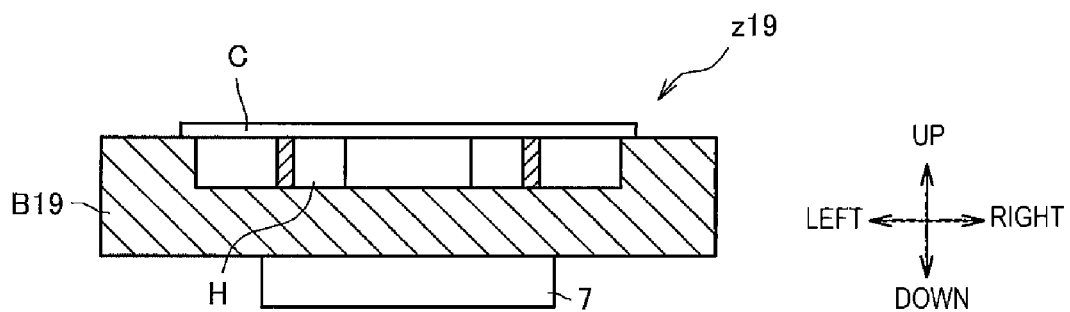
[FIG. 35]
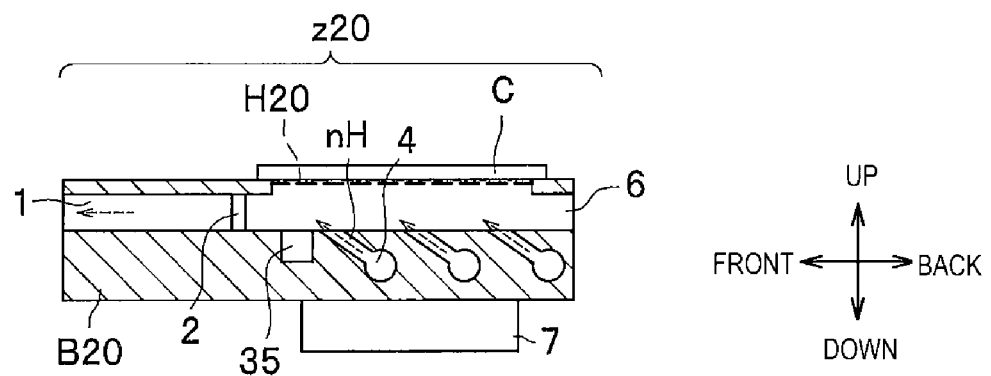

[FIG. 36]
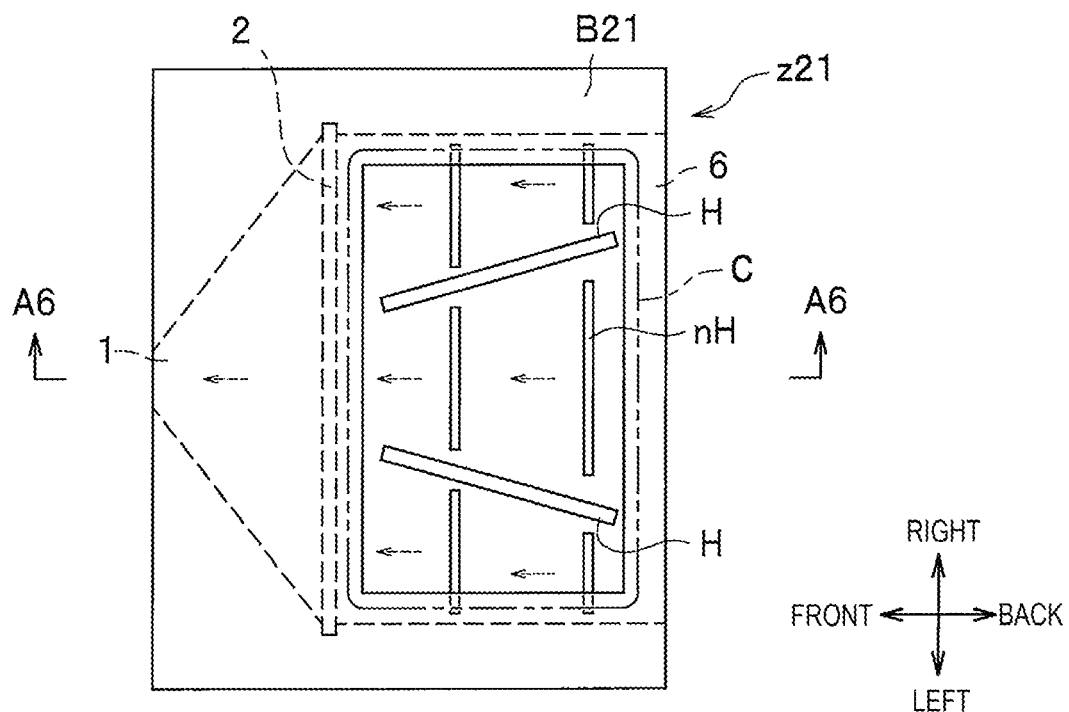
[FIG. 37]
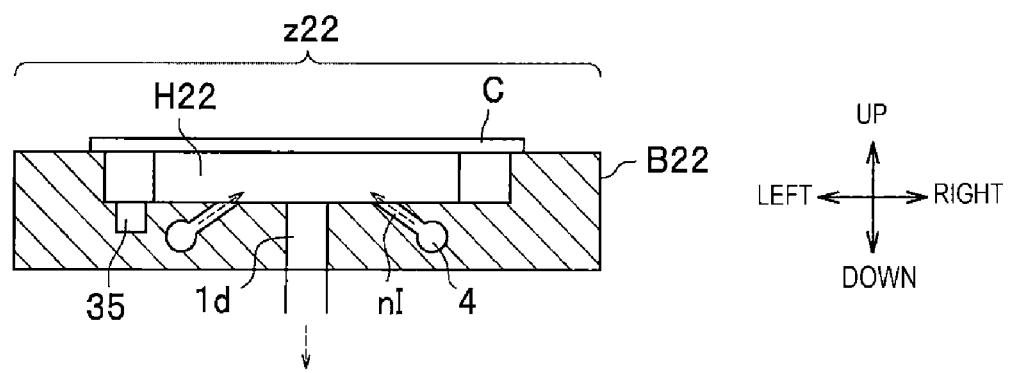

[FIG. 38]
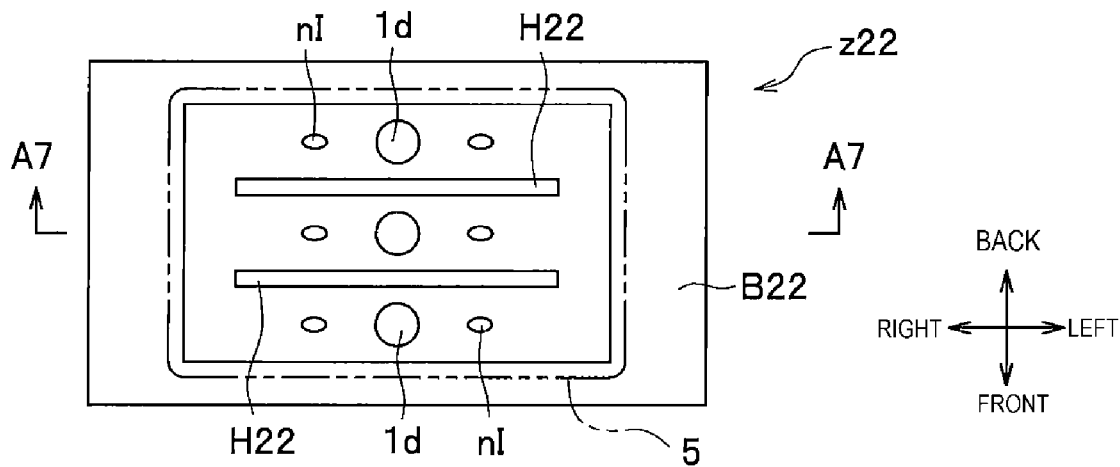
[FIG. 39]
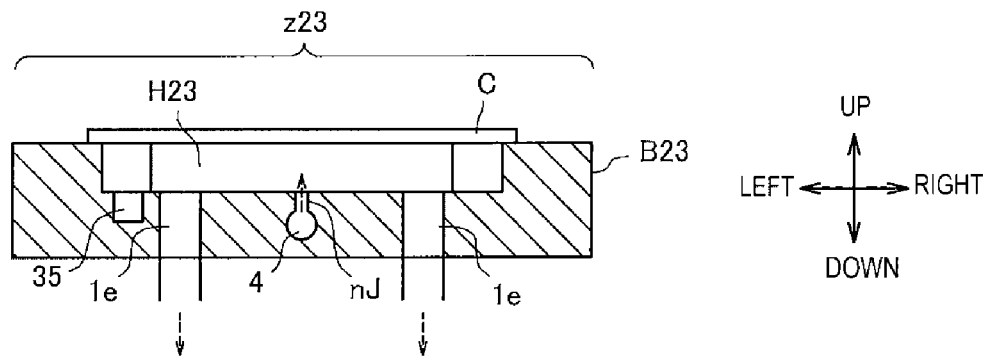
[FIG. 40]
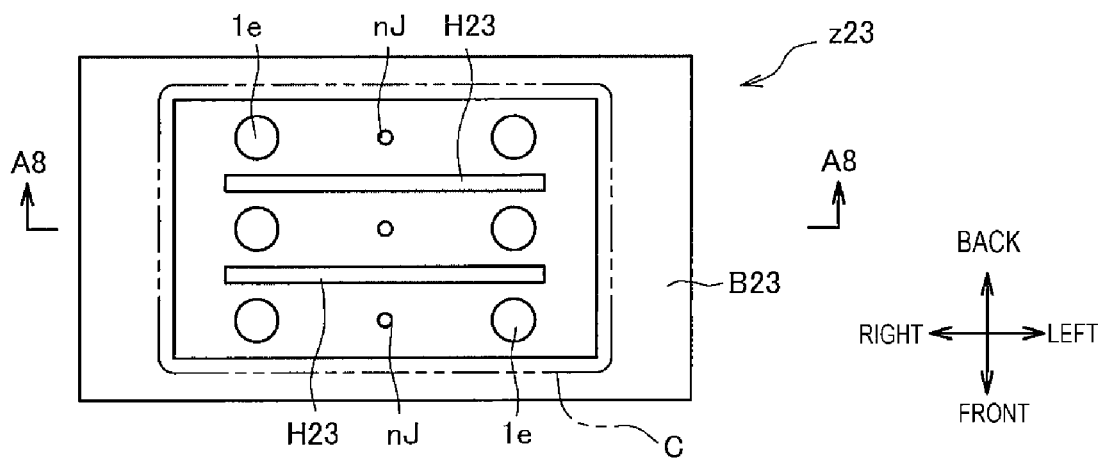

[FIG. 41]
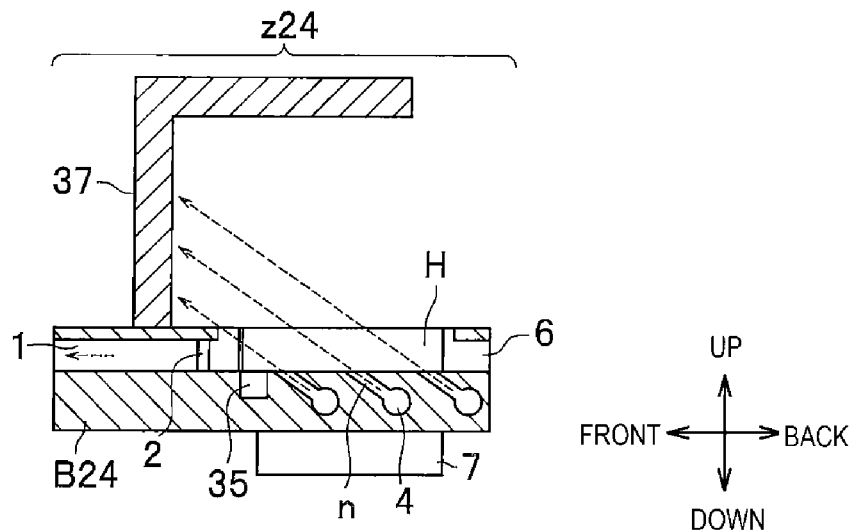
[FIG. 42]
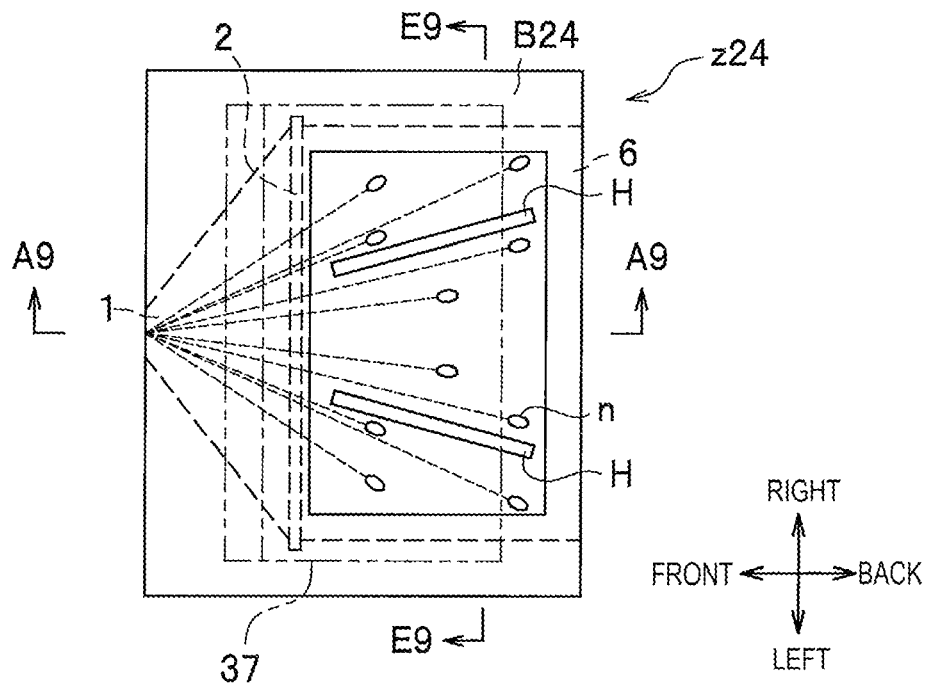

[FIG. 43]
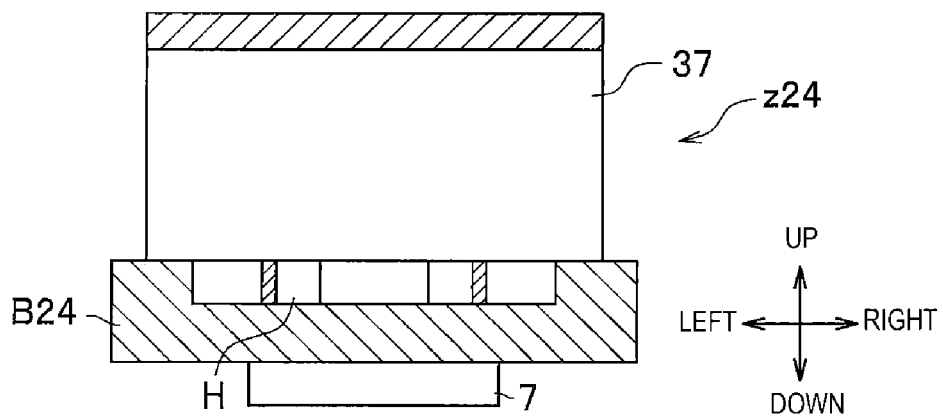
[FIG. 44]
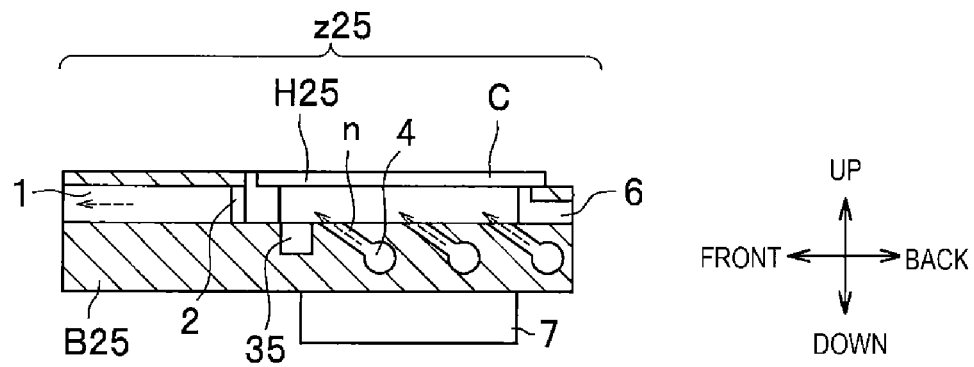

ADHERING SUBSTANCE COLLECTING DEVICE AND INSPECTION SYSTEM

TECHNICAL FIELD

The present invention relates to a technique of an adhering substance collecting device that detaches and collects substances adhering to an inspection object and an inspection system.

BACKGROUND ART

In an optical field, an environmental field, or the like, adhering substances adhering to an inspection object are analyzed. In particular, in the environmental field, in order to grasp a state of environmental pollution, there is a demand for an analysis device that measures the adhering substances quickly, in real time, and with high sensitivity. In addition, in an industrial field, for a purpose of management and quality control of a production process, there is a demand for an analysis device that measures adhering substance components adhering to an industrial product quickly, in real time, and with high sensitivity.

For example, Patent Literature 1 discloses an analysis device "comprising: a blowing unit that detaches a sample adhering to a target; a suction unit that sucks the sample detached from the target; a particulate capturing unit that concentrates and captures the sucked sample; an ion source unit that introduces the sample from the particulate capturing unit for ionization; a mass analysis unit that performs mass analysis of ions generated at the ion source unit; a control unit that controls the ion source unit and the mass analysis unit; a database unit that holds mass spectrum data derived from detection target substances; and a determination unit that compares a mass analysis result of the sample by the mass analysis unit with the mass spectrum data held at the database unit, thus determining presence or absence of the detection target substances" and an analysis method (refer to claim 1).

Further, for example, Patent Literature 2 discloses an analysis device "comprising: an authentication unit that authenticates a target including an opening part and an internal space for inserting the target; a blowing unit that generates injection airflow from at least two different directions with respect to the target; a recovery opening that is connected to the internal space of the authentication unit and collects gas and/or particulates detached from the object; a suction unit that sucks gas and/or particulates detached from the object; a flow control unit that controls the injection airflow of the blowing unit and suction of the suction unit; a particulate capturing unit that concentrates and captures target substances to be detected, contained in the sucked gas and/or particulate; an analysis unit that analyzes the target substances to be detected, introduced from the particulate capturing unit; and an analysis determination control unit that determines presence or absence of the target substances to be detected, from a result analyzed with the analysis unit" (refer to claim 1).

CITATION LIST

Patent Literature

PTL 1: PCT/JP2011/075666
PTL 2: PCT/JP2014/071718

SUMMARY OF INVENTION

Technical Problem

Conventionally, in a case of collecting the adhering substances adhering to the inspection object and analyzing the collected adhering substances quickly and in real time, there has been a problem that a positional relationship between the inspection object and the ejection opening that injects the airflow is not constant, and detachment efficiency and collection efficiency are not stable.

The invention has been made in view of such a background, and in an attempt to solve a problem of stably detach substances from the inspection object.

Solution to Problem

In order to solve the problem described above, the invention provides an adhering substance collecting device that includes: a surface equipped with a plurality of ejection openings each of which is configured to eject gas; a spacer configured to separate an object from the surface; and a recovery opening configured to recover the gas ejected toward the object. Adhering substances adhering to the object are collected from the gas.

Other solutions will be described in embodiments.

Advantageous Effect

In the invention, substances can be stably detached from the inspection object.

BRIEF DESCRIPTION OF DRAWINGS

FIG. 1 is a schematic cross-sectional view of an adhering substance collecting device according to a first embodiment.

FIG. 2 is a view illustrating a positional relationship between an ejection opening, an inspection object, a supporting portion, and a recovery opening when the adhering substance collecting device is seen from the top, according to the first embodiment.

FIG. 3 is a view of the adhering substance collecting device seen from an insertion opening side of the inspection object, according to the first embodiment.

FIG. 4 is a diagram illustrating a configuration of an airflow supply source system according to the first embodiment.

FIG. 5 is a diagram illustrating an entire configuration of an inspection system in this embodiment.

FIG. 6 is a diagram illustrating time change of a signal obtained by the inspection system.

FIG. 7 is a diagram illustrating an example of a processing procedure of the inspection system according to the first embodiment.

FIG. 8 is a view illustrating a positional relationship between an ejection opening, an inspection object, a supporting portion, and a recovery opening when the adhering substance collecting device is seen from the top, according to a second embodiment.

FIG. 9 is a diagram illustrating injection timing in each group.

FIG. 10 is a diagram illustrating flow of airflow in the adhering substance collecting device according to the second embodiment.

FIG. 11 is a diagram illustrating an example of an airflow supply source system according to a third embodiment.

FIG. 12 is a view (first) illustrating a positional relationship between an ejection opening, an inspection object, a supporting portion, and a recovery opening when a top cross-sectional view of an adhering substance collecting device is seen from the top, according to a fourth embodiment.

FIG. 13 is a view (second) illustrating another positional relationship between the ejection opening, an inspection object, a supporting portion, and a recovery opening when a top cross-sectional view of the adhering substance collecting device is seen from the top, according to the fourth embodiment.

FIG. 14 is a view (third) illustrating a still another positional relationship between an ejection opening, an inspection object, a supporting portion, and a recovery opening when a top cross-sectional view of the adhering substance collecting device according to the fourth embodiment is seen from the top.

FIG. 15 is a view (fourth) illustrating a yet another positional relationship between an ejection opening, an inspection object, a supporting portion, and a recovery opening when a top cross-sectional view of the adhering substance collecting device according to the fourth embodiment is seen from the top.

FIG. 16 is a view (first) illustrating a positional relationship between an ejection opening, an inspection object, a supporting portion, and a recovery opening when the adhering substance collecting device according to the second embodiment is seen from the top, according to a fifth embodiment.

FIG. 17 is a view (second) illustrating another positional relationship between an ejection opening, an inspection object, a supporting portion, and a recovery opening when the adhering substance collecting device according to the second embodiment is seen from the top, according to a fifth embodiment.

FIG. 18 is a view (third) illustrating a still another positional relationship between an ejection opening, an inspection object, a supporting portion, and a recovery opening when the adhering substance collecting device according to the second embodiment according to a fifth embodiment is seen from the top.

FIG. 19 is a view (fourth) illustrating a yet another positional relationship between an ejection opening, an inspection object, a supporting portion, and a recovery opening when the adhering substance collecting device according to the second embodiment according to a fifth embodiment is seen from the top.

FIG. 20 is a view (first) of an adhering substance collecting device seen from an insertion opening side, according to a sixth embodiment.

FIG. 21 is a view (second) of another adhering substance collecting device seen from an insertion opening side, according to the sixth embodiment.

FIG. 22 is a view (third) of a still another adhering substance collecting device seen from an insertion opening side, according to the sixth embodiment.

FIG. 23 is a view (fourth) of a yet another adhering substance collecting device seen from an insertion opening side, according to the sixth embodiment.

FIG. 24 is a schematic cross-sectional view of an adhering substance collecting device according to a seventh embodiment.

FIG. 25 is a view illustrating a positional relationship between an ejection opening, an inspection object, a supporting portion, and a recovery opening when an adhering substance collecting device is seen from the top, according to an eighth embodiment.

FIG. 26 is a schematic cross-sectional view of an adhering substance collecting device according to a ninth embodiment.

FIG. 27 is a view illustrating a positional relationship between an ejection opening and a recovery opening when the adhering substance collecting device is seen from the top, according to the ninth embodiment.

FIG. 28 is a schematic cross-sectional view of another example of an adhering substance collecting device according to the ninth embodiment.

FIG. 29 is a view illustrating a positional relationship between an ejection opening and a recovery opening when a still another example of the adhering substance collecting device is seen from the top, according to the ninth embodiment.

FIG. 30 is a view illustrating a positional relationship between an ejection opening, a recovery opening, and a supporting portion when an adhering substance collecting device is seen from the top, according to a tenth embodiment.

FIG. 31 is a schematic cross-sectional view of the adhering substance collecting device according to the tenth embodiment.

FIG. 32 is a schematic cross-sectional view of an adhering substance collecting device according to an eleventh embodiment.

FIG. 33 is a top view of the adhering substance collecting device according to the eleventh embodiment.

FIG. 34 is another schematic cross-sectional view of the adhering substance collecting device according to the eleventh embodiment.

FIG. 35 is a schematic cross-sectional view (first) illustrating another example of an adhering substance collecting device according to the eleventh embodiment.

FIG. 36 is a top view (first) of a still another example of the adhering substance collecting device according to the eleventh embodiment.

FIG. 37 is a schematic cross-sectional view (second) of the still another example of the adhering substance collecting device according to the eleventh embodiment.

FIG. 38 is a top view (second) of the still another example of the adhering substance collecting device according to the eleventh embodiment.

FIG. 39 is a schematic cross-sectional view (third) of a yet another example of an adhering substance collecting device according to the eleventh embodiment.

FIG. 40 is a top view (third) of the yet another example of the adhering substance collecting device according to the eleventh embodiment.

FIG. 41 is a schematic cross-sectional view of an adhering substance collecting device according to a twelfth embodiment.

FIG. 42 is a top view of the adhering substance collecting device according to the twelfth embodiment.

FIG. 43 is a schematic cross-sectional view of the adhering substance collecting device according to the twelfth embodiment.

FIG. 44 is a schematic cross-sectional view of an adhering substance collecting device according to a thirteenth embodiment.

DESCRIPTION OF EMBODIMENTS

Hereinafter, modes for carrying out the invention (referred to as "embodiments") will be described with reference to the attached drawings. Although specific examples according to a principle of the invention are shown in the present embodiment, they are for the purpose of understanding the invention and are never used to interpret the invention in a limited way. Variations due to combinations and substitutions of the following embodiments and known techniques are also contained in the scope of the invention. In all drawings for illustrating the embodiments, elements having the same functions are denoted by the same reference numerals, and repeated descriptions thereof will be omitted.

First Embodiment

First, a first embodiment of the present invention will be described with reference to FIG. 1 to FIG. 7.
(Adhering Substance Collecting Device)

FIG. 1 is a schematic cross-sectional view of an adhering substance collecting device. FIG. 2 is a view illustrating a positional relationship between an ejection opening, an inspection object, a supporting portion, and a recovery opening when the adhering substance collecting device (see FIG. 1) according to the first embodiment is seen from the top. FIG. 3 is a view of the adhering substance collecting device (see FIG. 1) seen from an insertion opening side (a back side of FIG. 1) of the inspection object, according to the first embodiment.

FIG. 1 illustrates an A1-A1 cross section in FIG. 2 and FIG. 3, and FIG. 2 illustrates a D1-D1 cross section in FIG. 1 and FIG. 3. In FIG. 1, the nozzle n is hidden in the housing B originally, but is illustrated as a cross section for conceptually easy understanding. Further, in FIG. 1, five nozzles n are to be displayed originally, but only three are illustrated for avoiding complicated drawings. The same applies to the following drawings.

FIG. 1 and FIG. 2 illustrate a state in which an inspection object (object) C is during insertion. Even in the following drawings, a state of the inspection object C during insertion is illustrated in the same drawing.

As illustrated in FIG. 1 and FIG. 3, pair of supporting portions (spacers) H is provided on an upper and a lower surfaces of an internal space in which the ejection openings n are arranged in an adhering substance collecting device (an adhering substance collecting unit) z. The supporting portion H has a protruded structure, that is, a rib shape.

In addition, an inspection system w (see FIG. 5) according to the first embodiment ejects airflow (gas) to both surfaces of the inspection object C such as an integrated circuit (IC) card and a magnetic card to collect adhering substances adhering to the inspection object C. The inspection system w performs authentication when the inspection object C is inserted into the adhering substance collecting device z, and acquires data on the authentication. The authentication data is written in an IC chip, a magnetic medium, a barcode, and a two-dimensional code embedded in the inspection object C, or attached to a surface thereof, or printed thereon.

Then, the inspection system w authenticates the inspection object C based on the authentication data.

At this time, a positional relationship between the inspection object C and the ejection opening n, which serves as an ejection opening that ejects airflow by the supporting portion H arranged in the adhering substance collecting device z, is constant in each inspection. Thus, adhering substances adhering to the inspection object C can be collected stably. The height of the supporting portion H is preferably about 2 mm to 3 mm.

In the inspection system w proposed in the present embodiment, the adhering substance collecting device z also serves as a card reader, and is applied as, for example, an authentication machine for opening and closing a door of an exit and entrance at an important facility or the like. In this case, it is possible to have a function of analyzing whether or not adhering substances adhering to the inspection object C such as the IC card are hazardous substances such as an explosive or the like quickly in real time in order to check presence or absence and trace of the hazardous substances of an inspection subject. The following embodiments can also be applied to, besides the exit and entrance, a security gate of an important facility or the like, a boarding gate of an airport, a ship, or the like, an automatic ticket gate, a baggage inspection field gate, a deposited baggage inspection field gate, an entrance and exit ticket gate of an amusement facility, and the like.

As illustrated in FIG. 2, in the adhering substance collecting device z according to the present embodiment, ten ejection openings n are arranged on the lower surface of the internal space of the housing B. Since the ejection openings n are arranged on the upper and lower surfaces of the internal space of the housing B, 20 units of the ejection openings n are used in the present embodiment. Airflow is ejected at about 200 L/min from the ejection opening n.

Although the ejection openings n are assumed to be arranged in a vertically symmetrical shape, but may be arranged vertically asymmetrically. When the ejection openings n are arranged in the vertically symmetrical shape, airflow is ejected symmetrically above and below the inspection object C, and therefore, the inspection object C is stably placed inside the housing B.

In the present embodiment, the inspection object C includes an IC card, a magnetic card, a name card, and a cardholder capable of holding one or more of those cards, but the invention is not limited thereto. For example, the invention can also be applied to a mobile phone, a mobile terminal, a ticket, a passport, and the like. In this embodiment, since a card holder having a depth of about 50 mm, a width of about 100 mm, and a thickness of about 5 mm is used as a target, dimensions of the insertion opening 6 is designed to be about 120 mm in width and 15 mm in height. However, it is to be easily understood that the invention is not limited to the dimensions.

In the present embodiment, as illustrated in FIG. 1, when the inspection object C is inserted into the internal space formed by the housing B, injection of airflow by the ejection openings n is started, and the inspection is thereby started. Adhering substances can be detached and collected from the upper and lower surfaces of the inspection object C by the airflow injected from the ejection openings n.

Here, a broken line arrow illustrated in FIG. 1 and broken lines illustrated in FIG. 2 indicate streams of the airflow. A solid bold arrow illustrated in FIG. 1 indicates an insertion direction of the inspection object C. The same applies to the following drawings unless otherwise specified.

As illustrated in FIG. 1 and FIG. 2, the airflow injected from the ejection openings n collides with the inspection object C and then flows toward the recovery opening 1.

Here, a periphery of the inspection object C other than the insertion opening 6 inserting into the inspection object C and the recovery opening 1 collecting adhering substances is covered with the housing B. Thus, the detached adhering substances are efficiently collected from the recovery opening 1 without scattering to the outside.

As illustrated in FIG. 1 and FIG. 2, the recovery opening 1 is arranged at a part farther away from a front side of the supporting portion H in a longitudinal direction thereof. The insertion opening 6 is arranged at a part on the front side of the supporting portion H. The supporting portion H restricts a change of a distance in a height direction between the inspection object C and the ejection opening n. That is, the distance between the inspection object C and the ejection opening n is maintained at a certain distance or larger by the supporting portion H.

Although the supporting portion H has a rectangular cross section in FIG. 1, a shape thereof such as an arc shape is not specifically limited as long as the distance between the inspection object C and the ejection opening n can be restricted.

As described above, the supporting portion H is structured to have a predetermined height from the surface of the internal space of the housing B.

As illustrated in FIG. 1 and FIG. 3, another supporting portion H is provided on the upper surface of the internal space of the housing B. By doing so, it is possible to maintain the distance between the inspection object C and the ejection opening n installed on the upper surface of the internal space of the housing B at a predetermined distance or larger. For example, as will be described later, when injection timing of the ejection opening n on the upper surface of the internal space of the housing B and the ejection opening n on the lower surface of the internal space of the housing B is made different from each other, the distance between the ejection opening n on the inner space and the upper surface of the housing B and the inspection object C can be maintained at a predetermined distance or larger.

If the supporting portion H is omitted, for example, when an inspection subject introduces the inspection object C so as to come in contact with the upper surface of the internal space of the housing B, the airflow from the upper surface is blocked. Therefore, the adhering substances adhering to the upper surface of the inspection object C cannot be detached and collected. In addition, the adhering substances may adhere to the upper surface of the internal space of the housing B and becomes carry-over. In this case, the carry-over may be detected in the next inspection. The same applies to a case where the inspection subject introduces the inspection object C so as to come in contact with the lower surface of the internal space of the adhering substance collecting device z.

As illustrated in FIG. 2, in the present embodiment, the recovery opening 1 is formed narrower than the insertion opening 6. As described above, each broken line in FIG. 2 indicates a direction of the airflow.

As illustrated in FIG. 2, the ejection openings n are installed so as to be directed to the recovery opening 1. By installing the ejection openings n as described above, the adhering substances detached from the inspection object C can be efficiently collected. Further, as illustrated in FIG. 2, two (a pair of) supporting portions H are installed such that a distance between each other decreases toward the recovery opening 1. Accordingly, the supporting portion H also has a function of smoothly transporting airflow and the detached adhering substances to the recovery opening 1 efficiently.

Further, the ejection openings n are present so as to avoid the supporting portion H. The ejection openings n are installed such that airflow does not collide with the supporting portion H and is efficiently directed to the recovery opening 1. Accordingly, it is possible to prevent the airflow from interfering due to the supporting portion H. As indicated by the broken line in FIG. 2, the ejection openings n are arranged so as not to overlap the airflow ejected from the ejection openings n. Accordingly, it is possible to prevent the airflow from interfering with each other. The supporting portion H is also arranged in a state of being inclined toward the recovery opening 1. This contributes to not blocking streams of the airflow and of the detached adhering substances. Accordingly, the supporting portion H also has a function of transporting the airflow and the detached adhering substances to the recovery opening 1 efficiently.

As illustrated in FIG. 1, the ejection openings n are inclined also with respect to the vertical direction. The angle is generally in a range of about 15° to 90° with respect to the vertical direction (90° is at right angles to the inspection object C), and is preferably 30° to 45°. A shape of the ejection opening n may be not only a substantially round shape, but also an ellipse, a square, a rectangle, or the like. A distance between a tip of the ejection opening n and the inspection object C is limited by the height of the supporting portion H. As the height of the supporting portion H lowers, the distance in the height direction between the ejection opening n and the inspection object C decreases. A gas velocity of the airflow injected from the ejection opening n decreases as a distance from the ejection opening n increases. At this time, since dynamic pressure acting on adhering substances by the airflow is proportional to a square of the gas velocity, the faster the gas velocity of the airflow, the higher the dynamic pressure acting on the adhering substances. That is, the closer the distance between the ejection opening n and the adhering substances, the higher the dynamic pressure. However, in a case where the inspection object C is uneven when the height of the supporting portion H is too low, the uneven portion may rub against the upper and lower surfaces of the internal space of the housing B, so it is preferable to have a moderate height.

It is known that there is a region in which a gas velocity in the airflow ejected from the ejection opening n does not decrease from a gas velocity at an outlet of the ejection opening n, which is called a potential core region. The distance between the inspection object C and the ejection opening n is preferably designed so as to be within the potential core region in order to efficiently detach the adhering substances while making the distance between the ejection opening n and the inspection object C spaced apart to some extent. For example, when the ejection opening n has a substantially round shape, the potential core region is from the tip of the ejection opening n to a distance of about 5 to 8 times the ejection diameter. Assuming that the potential core region is six times the ejection diameter, the potential core region extends to a position 9 mm from the tip of the ejection opening n when the ejection diameter is 1.5 mm. When the angle of the ejection opening n with respect to the vertical direction is θ, a distance in the height direction between the inspection object C and the ejection opening n is preferably designed to be within 9 sin θ mm. For example, when θ=30°, the distance is 4.5 mm. The height of the vertically arranged supporting portions H is 2 mm. When the inspection object C is arranged between the upper and lower supporting portions H, a gap of 1 mm is provided each between the inspection object C and the upper and lower supporting portions H. Then, when the inspection object C is placed on the lower side supporting portion H, a distance in the height direction between the surface of the inspection object C and the upper and lower ejection openings n is between 2 mm and 4 mm. By adjusting such that the supporting portion H is arranged as described above and the height of the supporting portion H is in the potential core region, more specifically, the potential core region length× sin θ, it is possible to stabilize an influence of the airflow on the surface of the inspection object C. This makes it possible to stabilize detachment of the adhering substances and reduce dispersion of inspection results.

As illustrated in FIG. 3, in the present embodiment, the height of the upper and lower supporting portions H are the same. However, it is not necessarily required and the vertical height may be different from each other.

The supporting portion H may have an upward or a downward inclination in the front-back direction.

As illustrated in FIG. 1 and FIG. 3, in the present embodiment, an authentication device 7 is installed in a lower portion of the housing B of the adhering substance collecting device z. When the inspection object C is, for example, an IC card, contents of the IC card is authenticated by the authentication device 7. The authentication device 7 has a prescribed authenticatable distance range, and the height of the supporting portion H may also be limited by the distance range.

As illustrated in FIG. 1, an infrared sensor 5 is provided in the adhering substance collecting device z. The infrared sensor 5 includes an infrared sensor light emitter 5a and an infrared sensor light receiver 5b. A broken line L indicates infrared light emitted from the infrared sensor light emitter 5a. When the inspection object C is inserted into the adhering substance collecting device z and the infrared light L is blocked, the infrared sensor light receiver 5b detects the block of the infrared light L. Accordingly, the insertion of the inspection object C is detected. The infrared sensor light emitter 5a and the infrared sensor receiver 5b may be provided upside down. The infrared sensor light emitter 5a and the infrared sensor light receiver 5b may be installed obliquely as long as at a position where the insertion of the inspection object C is detected. A plurality of units of each of the infrared sensor light emitter 5a and the infrared sensor light receiver 5b may be installed. For example, the infrared sensor light emitter 5a and the infrared sensor receiver 5b may be installed near an insertion opening 6 in addition to positions of the infrared sensor light emitter 5a and the infrared sensor receiver 5b illustrated in FIG. 1. When the infrared sensor light emitter 5a and the infrared sensor light receiver 5b are installed near the insertion opening 6, it is possible to detect that the inspection object C has started to be inserted.

Although the housing B may be non-transparent or transparent, it is preferable for the inspection subject to easily insert the inspection object C into the adhering substance collecting device z if the housing B is transparent.

As illustrated in FIG. 1 and FIG. 2, a coarse mesh filter 2 is provided in front of the recovery opening 1. The coarse mesh filter 2 is to prevent large dust from entering the recovery opening 1. As the coarse mesh filter 2, for example, a stainless gauze mesh (a mesh opening of 0.5 mm, a hole density of 50%) is used. The coarse mesh filter 2 can be exchanged, and can be cleaned and reused or replaced with a new one when dust is choked.

As illustrated in FIG. 1, the ejection opening n is connected to a pipe 4 for an ejection opening n that supplies airflow to the ejection opening n. The pipe 4 is connected to an airflow supply source (described later) outside the housing B. In FIG. 1, the pipe 4 extends to a front direction of the with respect to the plane of the figure. The pipes 4 connected to the ejection openings n respectively may extend to the outside and be connected to the airflow supply source. Alternatively, the pipes 4 connected to the plurality of ejection openings n may be integrated into one in the housing B, and then move out to the outside of the housing B and be connected to the airflow apply source.

(Inspection System)

FIG. 4 is a diagram illustrating a configuration of an airflow supply source system according to the first embodiment.

In the airflow apply source system Y illustrated in FIG. 4, the pipes 4 connected to 20 units of the ejection openings n (see FIG. 1) arranged in the adhering substance collecting device z are made up of four pipes 12 in the housing B, and then connected to a pulse valve 13. The pulse valve 13 is connected to a pressure controller 15 via a pipe 14. Further, the pressure controller 15 is connected to a compressor 17 via a pipe 16. In the compressor 17, for example, pressure is improved to about 0.7 MPa. Pressure of airflow supplied to the ejection opening n is further adjusted with the pressure controller 15.

The airflow apply source system Y corresponds to the above-described airflow apply source.

The pulse valve 13 is normally in a closed state, and supplies compressed airflow to the ejection opening n in a pulse manner by opening for about 0.1 seconds.

In the example illustrated in FIG. 4, one pressure controller 15 and one compressor 17 are connected to the four pulse valves 13, but the pressure controller 15 and the compressor 17 may be installed individually for each pulse valve 13. In particular, by arranging the pressure controller 15 for each pulse valve 13, the pressure of the airflow supplied via a position of the ejection opening n can be changed.

An air reservoir (not illustrated) may be provided between the pulse valve 13 and the compressor 17. For example, when a flow rate passing through the pulse valve 13 is 60 L/min, 100 mL of airflow is discharged from the ejection opening n in 0.1 seconds. In a case of plural times of injection, the airflow is discharged accordingly. Therefore, a necessary amount of compressed air is reserved in the air reservoir.

FIG. 5 is a diagram illustrating an entire configuration of an inspection system in this embodiment.

An inspection system w is assumed to be a security gate system capable of analyzing adhering substances adhering to the surface of the inspection object C and authenticating the inspection object C. In particular, it is an object to detect hazardous substances such as explosives. The inspection system w includes the adhering substance collecting device z, the authentication device 7, the infrared sensor 5, the pulse valve 13, the pressure controller 15, the compressor 17, a human sensor 18, and an attached substance concentration device 19. The inspection system w further includes an analysis device 40, an suction device 21, a control/data processing device 25, a result display device 26, and a gate 27. Among these, the pulse valve 13, the pressure controller 15, and the compressor 17 constitute the airflow apply source system Y illustrated in FIG. 4. Examples of the human sensor 18 may include an infrared sensor and an ultrasonic sensor.

The adhering substance concentration device 19 includes a cyclone capturing unit 20, a heater 22, a primary filter 23, and a secondary filter 24. The inspection system w is not necessarily limited to the configuration illustrated in FIG. 5, and only a representative example is illustrated in FIG. 5.

Since the concentration of the adhering substances detached by the adhering substance collecting device z in the air is very low, it is difficult to perform analysis by the analysis device 40 as it is. Therefore, the adhering substance concentration device 19 is provided between the analysis device 40 and the adhering substance collecting device z.

Thus, a concentration of the detached adhering substances can be increased, and analysis by the analysis device 40 can be performed.

The cyclone capturing unit 20 separates and concentrates the adhering substances detached by the airflow. A mass spectrometer and an ion mobility analysis device, which are typical analysis devices, generally can suck a sample flow rate of only 1 L/min or less. When only 1 L/min of 200 L/min of airflow is sucked, inspection sensitivity is reduced to 1/200.

Therefore, as in the present embodiment, since the cyclone capturing unit 20 is installed between the adhering substance collecting device z and the analysis device 40, the adhering substances are separated and concentrated from the airflow. The cyclone capturing unit 20 can capture a sample having a certain particle size and density or larger to a lower portion of the cyclone capturing unit 20 by using centrifugal force. For example, under certain conditions, adhering substances having a particle size of 1 μm or more rotationally move in the cyclone capturing unit 20 and are separated to an outer circumferential side of the cyclone capturing unit 20 by centrifugal force. A radius of rotation decreases toward a lower part of the cyclone capturing unit 20. The adhering substances other than those (a particle diameter less than 1 μm) is discharged together with the airflow by the intake device 21 from a central suction pipe 51. The minimum particle size (separation limit particle size) of the adhering substances separated from the airflow by the rotational motion varies depending on a configuration of the cyclone capturing unit 20 and an suction flow rate of the suction device 21.

For example, since an explosive particulate as a hazardous substance has a particle diameter of about 5 μm to 100 μm, it is preferable that particulates each having this particle diameter are collected. Not only explosive particulates but also substances adhering to the inspection object C may be detected, such as chemical agents, harmful substances, hazardous substances, combustible substances, biological agents, viruses, bacteria, genes, environmental substances, and the like.

The adhering substances captured at the lower part of the cyclone capturing unit 20 settle to the heater 22 as they are. The heater 22 is provided with a primary filter 23. The settled adhering substances are captured by the primary filter 23 and vaporize by being heated by the heater 22. The vaporized adhering substances pass through the secondary filter 24 and are introduced into the analysis device 40. In the adhering substance concentration device 19, it is only necessary that the detached adhering substances can be concentrated, and the cyclone capturing unit 20 may not be provided.

In order to improve an effect of the adhering substance concentration device 19, it is desirable that the suction flow rate of the adhering substance concentration device 19 is larger than the total flow rate of the airflow injected from the ejection openings n. For example, when the total flow rate of the injected airflow from the ejection openings n is 100 L/min, the suction flow rate of the cyclone capturing unit 20 is desirably 100 L/min or more. For example, when the suction flow rate of the cyclone capturing unit 20 is 150 L/min and the flow rate from the cyclone capturing unit 20 to the analysis device 40 is 0.5 L/min, the adhering substances captured by the cyclone capturing unit 20 are concentrated 300 times. In this way, by using the cyclone capturing unit 20 in the adhering substance concentration device 19, a concentration degree of the collected adhering substances can be improved, and accuracy of analysis can be improved.

The heater 22 heats the adhering substance at 200° C., for example. A temperature of the heater 22 may be any temperature at which the captured adhering substances can vaporize, and may be changed depending on components of the adhering substances to be inspected. A user can remove the primary filter 23 and the secondary filter 24. Accordingly, the user can clean and reuse the primary filter 23 and the secondary filter 24 and exchange them with new ones as necessary. Exchange of them can also be performed manually, but a predetermined automatic exchange device (not illustrated) may exchange the primary filter 23 and the secondary filter 24.

The primary filter 23 and the secondary filter 24 may have any filtration accuracy as long as particulates each having a particle size of 1 μm or more can be captured. For example, a stainless filter having a filtration accuracy of 1 μm to 50 μm can be used as the primary filter 23 and the secondary filter 24. A pipe 52 connecting the heater 22 and the analysis device 40 is also heated. This is to prevent molecules vaporized by the heater 22 from being adsorbed to an inner wall of the pipe 52. The secondary filter 24 is installed for the purpose of preventing the adhering substances not captured by the primary filter 23 from entering the analysis device 40. The pipe 52 between the heater 22 and the analysis device 40 is not necessarily required, and the heater 22 and the analysis device 40 may be directly connected. In this case, the secondary filter 24 is omitted.

For example, a wire type linear ion trap mass spectrometer can be used as the analysis device 40. In addition, a linear ion trap mass spectrometer, a quadrupole ion trap mass spectrometer, a quadrupole filter mass spectrometer, a triple quadrupole mass spectrometer, a time-of-flight mass spectrometer, a magnetic field type mass spectrometer, or the like may be applied as the analysis device 40. Alternatively, an ion mobility analysis device or the like may be used as the analysis device 40. A device that connects the ion mobility analysis device with the mass spectrometer can also be used. Further, a device using various light sources such as fluorescence, infrared rays, and ultraviolet rays may be used as the analysis device 40.

When these mass spectrometers are used as the analysis device 40, the control/data processing device 25 analyzes the mass spectrum measured with the analysis device 40 and specifies component identification and concentration of the adhering substances from the mass spectrum. The control/data processing device 25 stores a database in advance. In the database, a threshold for the component identification and concentration determination of the adhering substances is set. When a concentration of the detected components exceeds a prescribed threshold, the control/data processing device 25 performs positive determination. In this case, the presence or absence of the components detected with the result display device 26 may be displayed. The result display device 26 may be configured such that a monitoring center (not illustrated) in a remote place and information of the components detected by an observer are notified without displaying the result. In cooperation with the analysis result, closing of the gate 27, recording by a monitoring camera (not illustrated), recording of authentication data, and the like may be performed. In addition to the mass spectrometer, the adhering substances are analyzed by comparing with the database even in another analysis device 40 such as the ion mobility analysis device.

A dashed line in FIG. 5 indicates transmission/reception of information. As illustrated in FIG. 5, the control/data processing device 25 acquires information from the infrared sensor 5, the authentication device 7, the human sensor 18, and the analysis device 40. The control/data processing device 25 controls the pressure controller 15, the heater 22, the gate 22, the suction device 21, and the like based on the acquired information. The control/data processing device 25 displays an analysis result and the like in the analysis device 40 on the result display device 26.

(Time Change of Signal)

FIG. 6 is a diagram illustrating a time change of a signal obtained when a card holder to which a plastic explosive adheres in the configuration of FIG. 5 is used as an inspection object.

Here, a horizontal axis indicates time, and the airflow is injected at timing of time "0". The explosive detached by the airflow is collected, heated and vaporized, and intensity of the signal detected with the analysis device 40 is illustrated by a vertical axis. It can be seen that the signal peaks at about 3 seconds from the injection.

(Processing Procedure)

FIG. 7 is a diagram illustrating an example of a processing procedure of the inspection system according to the first embodiment. Appropriately, reference is made to FIG. 1 to FIG. 3 and FIG. 5.

First, when a person as an inspection subject approaches the device, the human sensor 18 detects the approach of the inspection subject (S101). Then, the cyclone capturing unit 20 starts suction (S102).

Although the cyclone capturing unit 20 may continuously perform suction, it is desirable to control the presence or absence of driving of the cyclone capturing unit 20 by the human sensor 18 in view of reducing power consumption, preventing mixing of useless dust, and the like.

Subsequently, the inspection subject inserts the inspection object C into the insertion opening 6 of the adhering substance collecting device z (S103).

Then, the infrared sensor 5 detects the insertion of the inspection object C (S111), and the airflow is injected from the ejection opening n (S112).

The adhering substances are detached from the inspection object C by the injected airflow, and are collected via the recovery opening 1 (S113).

The collected adhering substances are concentrated by the adhering substance concentration device 19 (S114), and then heated and vaporized by the heater 22 (S115).

Then, the heated and vaporized adhering substances are analyzed by the analysis device 40 (S116). The analysis device 40 transmits an analysis result to the control/data processing device 25.

At the same time with the processing from the step S111 to the step S116, the authentication device 7 acquires authentication information from the inspection object C (S121). The processing from the step S111 to the step S116 and processing of the step S121 may not necessarily be performed in parallel, but, by doing so, inspection throughput is improved.

The authentication device 7 transmits the acquired authentication information to the control/data processing device 25.

Then, in a step S131, the control/data processing device 25 determines whether or not the adhering substances are hazardous substances or whether or not the authentication has failed. The control/data processing device 25 determines whether or not the adhering substances are hazardous substances based on the analysis result transmitted from the analysis device 40. The control/data processing device 25 determines whether or not the authentication is approved based on the authentication information transmitted from the authentication device 7.

As a result of the step S131, when the adhering substances are determined as hazardous substances or the authentication fails (S131→Yes), the control/data processing device 25 does not open the gate 27 (non-opening) (S132).

As a result of the step S131, when the hazardous substances are not detected and the authentication is successful (S131→No), the control/data processing device 25 performs permission determination and opens the gate 27 (S133).

In the present embodiment, the gate 27 is assumed to be in a closed state in a normal state, but the gate 27 in the normal state may be in an open state. In this case, when the hazardous substances are detected or the authentication is not approved, the gate 27 is changed from the open state to the closed state.

Further, by displaying the analysis result on the result display device 26 as described in FIG. 5, contents of the analysis result may be notified to the inspection subject, or the contents of the analysis result may be notified only to a security guard in the remote place. For example, the control/data processing device 25 may notify the inspection subject of only permission/non-permission information (that is, the determination result of the step S131), and notify the guard of also a reason of permission/non-permission.

In a case where prevention of useless inspection is prioritized, the step S121 and authentication determination are performed first, and when the authentication is confirmed, the processing from the step S111 to the step S116 may be performed by injecting airflow at the ejection opening n.

According to the present embodiment, since the supporting portion H is provided in the housing B, the distance between the ejection opening n and the inspection object C can be prevented from being equal to or less than a predetermined distance. That is, pressure of airflow can be kept constant. That is, a positional relationship between the ejection opening that ejects the airflow and the inspection object can be maintained in a predetermined range.

By doing as described above, the adhering substances can be detached from the inspection object C stably.

Further, in a technique described in Patent Literature 1, the adhering substances can be detected at high speed, but the adhering substances adhering to a surface of the IC card opposite to a surface with which the injected airflow collides cannot be collected.

According to the present embodiment, the adhering substances adhering to both surfaces of the inspection object C can be collected.

The larger an area of the surface of the inspection object C with which airflow is made to collide, the more accurately the inspection can be performed. Airflow can collide with a wide region if the airflow is injected not in a pulse manner but continuously in a process in which the inspection object C is inserted or extracted.

As described above, as the distance from the ejection opening n increases, the velocity of the airflow decreases, and the detachment efficiency of the adhering substance decreases. When the airflow collides while the inspection object C is moved, a wide region of the surface of the inspection object C approaches the ejection opening n, which improves the detachment efficiency.

That is, since strength of the airflow varies depending on a position, if the inspection object C continuously collides with the airflow while moving in the housing B, a position having strong airflow collides with the entire surface of the inspection object C. This makes it possible to improve the collection efficiency of the adhering substances. The same applies to a case where the inspection object C is extracted.

Timing of inserting and extracting the inspection object C can be detected in such a manner that the infrared sensor 5 (see FIG. 1) is installed on a side of the insertion opening 6 and detects the timing.

Further, although it is assumed that the supporting portion H has a rectangular cross section, the cross section may be a triangle. By doing in this way, since a contact area between the supporting portion H and the inspection object C can be reduced, an area where the airflow collides with the inspection object C can be increased, and the collection efficiency of the adhering substances can be improved.

Second Embodiment

Next, a second embodiment of the invention will be described with reference to FIG. 8 to FIG. 10. In and after the second embodiment, since a configuration and a processing procedure of an inspection system are the same as those illustrated in FIG. 4, FIG. 5, and FIG. 7, description in and after the second embodiment will be omitted.

FIG. 8 is a view illustrating a positional relationship between an ejection opening, an inspection object, a supporting portion, and a recovery opening when the adhering substance collecting device according to the second embodiment is seen from the top (a figure corresponding to FIG. 2). FIG. 9 is a diagram illustrating injection timing in each group (later described). FIG. 10 is a diagram illustrating a stream of airflow in the adhering substance collecting device according to the second embodiment. In FIG. 8 and FIG. 9, same reference numerals are given to the same components as those in FIG. 2, and descriptions thereof are omitted where appropriate.

FIG. 8 and FIG. 9 are figures corresponding to a D1-D1 cross section in FIG. 1 and FIG. 3 (figures corresponding to FIG. 2).

In the second embodiment, the ejection openings n are grouped and airflow is injected at different timings for each group.

In the adhering substance collecting device z1 illustrated in FIG. 8, the ejection openings n provided on the upper surface of the internal space of the housing B are denoted by reference numerals n1 to n10, respectively. The ejection openings n provided on the lower surface of the internal space of the housing B are referred to as reference numerals n1$a$ to n10$a$. The ejection openings n1$a$ to n10$a$ installed on the lower surface of the internal space of the housing B are not illustrated in FIG. 8 and FIG. 10. The ejection openings n1 to n10 installed on the upper surface of the internal space of the housing B and the ejection openings n1$a$ to n10$a$ installed on the lower surface of the internal space of the housing B are installed face to face each other.

As described in FIG. 4, a plurality of pulse valves 13 are connected to a plurality of the ejection openings n. A plurality of the ejection openings n connected to the same one of the pulse valves 13 injects airflow at the same timing. Here, a plurality of the ejection openings n connected to the same pulse valve 13 are referred to as a group.

As a representative example, as illustrated in FIG. 8, one group is formed by the ejection openings n1 to n5. In the same way, another group is formed by the ejection openings n1$a$ to n5$a$. A still another group is formed by the ejection openings n6 to n10. A yet another group is formed by the ejection openings n6$a$ to n10$a$. The groups are referred to as groups G1 to G4, respectively. In FIG. 8, since being present on the lower surface side of the internal space of the housing B, the groups G2, G4 are not illustrated. By setting the pulse valves 13 connected to the groups G1 to G4 respectively to an open state for 0.1 second separately, the ejection openings n in the groups G1 to G4 inject airflow. At this time, as illustrated in FIG. 9, the groups G1 to G4 are controlled not to inject simultaneously. As illustrated in FIG. 9, the groups G1 and G2 are continuously injected without an interval. Then, after the ejection of the group G2, the ejection openings n of the groups G3 and G4 continuously inject airflow after an interval of 0.1 seconds. This is to prevent interference of the airflow.

In a case where airflow is injected in each of the groups G1 to G4 at the timing illustrated in FIG. 9, when a flow rate of the injected airflow is larger than a flow rate sucked at the recovery opening side, the airflow injected from the ejection opening n on a left side of the plane of FIG. 10 as the groups G1, G2 flows rightward in the same figure. Therefore, when the group G1 and the group G3 are continuously injected, there is a possibility that the airflow inconveniently collides within the internal space of the housing B.

This may reduce efficiency in which the detached adhering substances are transported to the recovery opening 1. In the second embodiment, such a problem is solved.

An injection sequence illustrated in FIG. 9 is a representative example and is not limited to the example. The groups G1, G2 and the groups G3, G4 may inject airflow simultaneously as long as the stream of the airflow is taken into account (see FIG. 10). However, in general, as the number of the ejection openings n for injection increases, the flow rate of the injected airflow increases. When a flow rate which is excessive compared with a suction flow rate on a side of the recovery opening 1 is injected, there is a possibility that the airflow is not collected in the recovery opening 1 and reflects on a side of the insertion opening 6 as illustrated in FIG. 10.

As described above, in this case, the collection efficiency of the adhering substances decreases. Therefore, ideally, it is desirable that the flow rate injected from the ejection opening n at a time is equal to or less than the suction flow rate on the side of the recovery opening 1. When the suction flow rate on the side of the recovery opening 1 is sufficiently larger than the injection flow rate from the ejection opening n, both the flow rate may be simultaneously injected from all the ejection openings n of n1 to n10 and n1$a$ to n10$a$. As the number of the ejection openings n for injection increases simultaneously, the inspection throughput improves.

In short, as more and more groups are created, an injection amount in one injection decreases. Therefore, when the suction flow rate on the side of the recovery opening 1 is small, the ejection openings n are grouped such that the injection amount in one injection does not exceed the suction flow rate on the side of the recovery opening 1. In a case where the suction flow rate on the side of the recovery opening 1 is sufficiently large, when the ejection openings n are grouped, the injection flow rate may decrease and the detachment force may decrease, and the grouping may not therefore be performed.

According to the adhering substance collecting device z1 according to the second embodiment, the ejection openings n are grouped and injected at different timings for each group, and thus, the injection amount at one time can be reduced. Accordingly, even when the suction flow rate on the side of the recovery opening 1 is small, the adhering substances can be reliably collected without the injection amount exceeding the suction flow rate on the side of the recovery opening 1.

Third Embodiment

FIG. 11 is a diagram illustrating an example of an airflow supply source system according to a third embodiment.

In an airflow apply source system Y1 according to the third embodiment, not a compressor 17 (a compressor) illustrated in FIG. 4 but an air blower 28 (a blower) is used as a supply source of airflow. In this case, a pressure controller 15 illustrated in FIG. 4 can also be omitted.

The air blower 28 is connected to a pipe 29 connected to the ejection opening n (see FIG. 1) in the adhering substance collecting device z, and airflow is made to flow from the air blower 28 to the ejection opening n. In an example illustrated in FIG. 11, one air blower 28 is connected to each pipe 29, but the pipes 29 may be together connected to one air blower 28.

According to the third embodiment, cost of the entire airflow apply source system Y1 can be reduced by using the pressure controller 15 which is less expensive than the compressor 17 and the air blower 28.

Fourth Embodiment

FIG. 12 to FIG. 15 are views illustrating a positional relationship between an ejection opening, an inspection object, a supporting portion, and a recovery opening when a top cross-sectional view of the adhering substance collecting device according to the fourth embodiment is seen from the top. FIG. 12 to FIG. 15 are drawings corresponding to a D1-D1 cross-sectional view in FIG. 1 and FIG. 3 (figures corresponding to FIG. 2). In FIG. 12 to FIG. 15, same reference numerals are given to components same as those in FIG. 2, and descriptions thereof are omitted.

The fourth embodiment shows an aspect in which a shape of the supporting portion H (see FIG. 1) is modified.

That is, as illustrated in the first embodiment, the supporting portion H does not necessarily have a parallelepiped shape, and may be a supporting portion H2 that protrudes in a hemispherical shape like that in the adhering substance collecting device z2 illustrated in FIG. 12. In this case, it is desirable to arrange the supporting portion H2 at a position not interfering with streams of airflow illustrated by broken lines. Further, the supporting portion H may be supporting portions H3, H4 having a parallelepiped shape divided into two or more like an adhering substance collecting device z3 illustrated in FIG. 13 and an adhering substance collecting device z4 illustrated in FIG. 14, respectively. For example, in FIG. 13, the supporting portion H3 is divided into two parts, a left side and a right side. Further, as illustrated in FIG. 13 and FIG. 14, the supporting portions H3, H4 are arranged radially with respect to the recovery opening 1, but are not limited to have such a shape. For example, as in the adhering substance collecting device z5 illustrated in FIG. 15, the supporting portion H5 may be arranged perpendicular to the recovery opening 1.

Here, the present embodiment is characterized in that there are ejection openings n which are injection openings injecting airflow and at least one of the supporting portions H2 to H5 that limits a distance relationship between the ejection opening n and the inspection object C. Therefore, the shape of the supporting portions H2 to H5 may be any shape as long as there is at least one of the supporting portions H2 to H5 that limits the distance relationship between the ejection opening n and the inspection object C.

For example, in addition to a hemispherical shape as illustrated in FIG. 12, a spherical shape or a pyramid shape may be used. Each of respective cross sections of the supporting portion H (see FIG. 1) and the supporting portions H3 to H5 may have a triangular or pentagonal shape instead of a square.

By forming a hemispherical shape like the supporting portions H2 illustrated in FIG. 12 and dividing the supporting portions H3 to H5 like the supporting portions H3 to H5 illustrated in FIG. 13 to FIG. 15, an area of the supporting portions H2 to H5 contacting with the inspection object C can be reduced. Accordingly, airflow can be applied to the inspection object C in a wider range than the adhering substance collecting devices z, z1 illustrated in the first and second embodiments. Therefore, the collection efficiency of the adhering substances can be improved.

Fifth Embodiment

FIG. 16 to FIG. 19 are views illustrating a positional relationship between an ejection opening, an inspection object, a supporting portion, and a recovery opening when the adhering substance collecting device according to the second embodiment is seen from the top, according to a fifth embodiment. FIG. 16 to FIG. 19 are drawings corresponding to a D1-D1 cross-sectional view in FIG. 1 and FIG. 3 (figures corresponding to FIG. 2). In FIG. 16 to FIG. 19, the same reference numerals are given to components same as those in FIG. 2, and descriptions thereof are omitted where appropriate.

The fifth embodiment shows an embodiment in which the shape of the ejection opening H (see FIG. 1) is modified.

In FIG. 16 to FIG. 19, dashed arrows indicate streams of airflow.

In examples illustrated in FIG. 16 to FIG. 19, a slit shape is adopted as a shape of an injection opening.

Like the adhering substance collecting device z6 illustrated in FIG. 16, a plurality of ejection openings nA each having a slit shape may be installed parallel to the insertion opening 6 and the recovery opening 1. Alternatively, as in an adhering substance collecting device z7 illustrated in FIG. 17, a plurality of ejection openings nB each having a slit shape may be installed so as to incline toward the recovery opening 1. Further, a plurality of the ejection openings n (see FIG. 1) are not necessarily required, and one ejection opening nC having a slit shape may be installed as in an adhering substance collecting apparatus z8 illustrated in FIG. 18. As illustrated in the fifth embodiment, when the ejection openings nA to nC each have a slit shape, airflow can be made to collide with the inspection object C in a wider range than the round ejection opening n in the first embodiment.

In addition, the ejection opening n is not necessarily required to have a linear shape, and may have an arc shape like an ejection opening nD of an adhering substance collecting device z9 illustrated in FIG. 19. By doing in this way, since airflow can be ejected such that the airflow converges from the ejection opening nC illustrated in FIG. 18 toward the recovery opening 1, the collection efficiency of the adhering substances can be improved.

By using the ejection opening nC illustrated in FIG. 18 and the ejection opening nD illustrated in FIG. 19, when the inspection object C is inserted into the adhering substance collecting devices z8 or z9 or extracted therefrom, since the entire surface of the inspection object C passes through the corresponding ejection openings nC or nD each having a slit shape, airflow can be made to collide with the entire surface of the inspection object C.

Sixth Embodiment

FIG. 20 to FIG. 23 are views of an adhering substance collecting device according to a sixth embodiment seen from an insertion opening side (figures corresponding to FIG. 3). In FIG. 20 to FIG. 23, the same reference numerals are given to components same as those in FIG. 2, and descriptions thereof are omitted where appropriate.

The sixth embodiment shows an embodiment in which the shape of the supporting portion H (see FIG. 1) is modified.

As illustrated in FIG. 1 and FIG. 3, it is not necessarily required that the supporting portions H are arranged on the upper and lower surfaces of the internal space of the housing B. For example, as in an adhering substance collecting device z10 illustrated in FIG. 20, the supporting portion H may be arranged only on the lower surface of the internal space of the housing B. Conversely, the supporting portion H may be arranged only on an upper portion of the upper surface of the internal space of the housing B (not illustrated).

When the width of the insertion opening 6 is narrower than the width of the inspection object C, the supporting portion H11 may be formed by providing a recessed portion on a side wall of the insertion opening 6 as in a housing B11 in the adhering substance collecting device z11 illustrated in FIG. 21.

As described above, the present embodiment is characterized in that the supporting portion H (see FIG. 1) is present for stabilizing a positional relationship between the inspection object C and the ejection opening n which is an ejection opening ejecting airflow, and a shape of the supporting portion H is not limited. Therefore, a supporting portion H12 may be formed by arranging a mesh between the inspection object C and the upper and lower surfaces of the internal space of the housing B in which the ejection openings n are arranged as in an adhering substance collecting device z12 illustrated in FIG. 22. Coarseness of the mesh in the supporting portion H12 is desirably coarse in a degree of not influencing airflow, and a mesh opening of 0.5 mm, a hole density of 50%, and the like are preferable. So far, the ejection openings n are arranged only on the upper and lower surfaces of the internal space of the housing B. The position of the ejection opening n is not limited to only the upper and lower surfaces of the internal space of the housing B, and may be arranged on a side surface. In this case, by arranging the supporting portion H13 also on the side surface as in the adhering substance collecting device z13 illustrated in FIG. 23, it is possible to stabilize the positional relationship between the ejection opening on the side surface (not illustrated) and the inspection object C.

In the adhering substance collecting devices z10 to z12 illustrated in FIG. 20 to FIG. 22, respectively, an area of the inspection object C where airflow hits can be increased compared with the adhering substance collecting device z according to the first embodiment. Therefore, the adhering substance collecting devices z10 to z12 according to the sixth embodiment can improve collection efficiency of the adhering substances compared with the adhering substance collecting device z according to the first embodiment.

In addition, in an adhering substance collecting device z13 illustrated in FIG. 23, since airflow is injected also from the side of the inspection object C, a wider range of adhering substances can be detached. Further, in the adhering substance collecting device z13 illustrated in FIG. 23, since it is possible to prevent the inspection object C from having a distance less than a predetermined distance even with respect to the ejection openings n installed on the side, it is possible to stably collect the adhering substances.

Seventh Embodiment

FIG. 24 is a schematic cross-sectional view of an adhering substance collecting device according to a seventh embodiment. FIG. 24 is a drawing corresponding to an A1-A1 cross-sectional view in FIG. 2 and FIG. 3 (a figure corresponding to FIG. 1). In FIG. 24, the same reference numerals are given to components same as those in FIG. 1, and descriptions thereof are omitted.

In an adhering substance collecting device z14 illustrated in FIG. 24, a shutter 32 is attached to the housing B. In FIG. 24, a solid bold arrow in up and down directions indicates an operation direction of the shutter 32. In the adhering substance collecting device z (see FIG. 1) in the first embodiment, the insertion opening 6 is in an open state. In contrast, in the adhering substance collecting device z14 illustrated in FIG. 24, the shutter 32 is attached to the insertion opening 6. Further, the shutter 32 is closed before and after insertion of the inspection object C, and thus, the insertion opening 6 is in a closed state. Unnecessary intake of dust can be avoided by closing the shutter 32 when an inspection subject is not near the adhering substance collecting device z14. When the human sensor 18 detects approach of the inspection subject, the shutter 32 is opened, and the shutter 32 is closed when insertion of the inspection object C is confirmed by the infrared sensor 5. The shutter 32 is closed after the inspection object C is inserted, and thus, the internal space of the housing B becomes a substantially airtight space. Accordingly, scattering of detached adhering substances is reduced, and the collection efficiency can be improved. In FIG. 24, the shutter 32 is provided on an upper side of the insertion opening 6, and the shutter 32 closes by moving downward. The present invention is not, however, limited thereto, and the shutter 32 may be provided on a lower side of the insertion opening 6, and the shutter 32 may close by moving upward.

In the seventh embodiment, the shutter 32 is provided in the adhering substance collecting device z according to the first embodiment. The present invention is not limited thereto, and the shutter 32 may be provided: in the adhering substance collecting devices z1 to z13 according to the second, and fourth to sixth embodiments; and adhering substance collecting devices z15 to z18 according to eighth to tenth embodiments to be described later.

Eighth Embodiment

FIG. 25 is a view illustrating a positional relationship between an ejection opening, an inspection object, a supporting portion, and a recovery opening when an adhering substance collecting device according to an eighth embodiment is seen from the top. FIG. 25 is a figure corresponding to a D1-D1 cross-sectional view in FIG. 1 and FIG. 3 (a figure corresponding to FIG. 2). In FIG. 25, the same reference numerals are given to components same as those in FIG. 2, and descriptions thereof are omitted.

In the adhering substance collecting device z15 illustrated in FIG. 25, a size of a recovery opening 1a in a housing B15 is larger than that of the insertion opening 6.

Even if a cyclone or an impactor is used as the adhering substance concentration device 19 (see FIG. 5), the size of the recovery opening 1 is smaller than that of the insertion opening 6 because an inlet size thereof is smaller than that of the general inspection object C. However, when the adhering substance concentration device 19 having a large inlet size is used, as illustrated in FIG. 25, the recovery opening 1a can be enlarged with respect to the insertion opening 6. By enlarging the recovery opening 1a with respect to the insertion opening 6, airflow injected from an ejection opening nE does not collide near the recovery opening 1a, and thus, collection efficiency of detached adhering substances can be improved.

Although the ejection opening nE has a slit shape in the example illustrated in FIG. 25, the ejection openings n, nA to nD, and the like illustrated in the first embodiment and the fifth embodiment are applicable. Arrangement, number, and shape of the supporting portion H15 are not limited to a shape and arrangement illustrated in FIG. 25, and any of the supporting portions H, H11 to H13, and the like illustrated in the first embodiment or the sixth embodiment are also applicable.

Ninth Embodiment

FIG. 26 to FIG. 29 are each a schematic view of an adhering substance collecting device according to a ninth embodiment. In FIG. 26 and FIG. 28, the same reference numerals are given to components same as those in FIG. 1, and descriptions thereof are omitted. In FIG. 27 to FIG. 29, the same reference numerals are attached to components same as those in FIG. 2, and descriptions thereof are omitted.

In the ninth embodiment, a positional relationship between the recovery opening 1 and the ejection opening n (see FIG. 1) is changed.

FIG. 26 is a schematic cross-sectional view of an adhering substance collecting device according to the ninth embodiment. FIG. 27 is a view illustrating a positional relationship between an ejection opening and a recovery opening when the adhering substance collecting device illustrated in FIG. 26 is seen from the top. FIG. 26 is a view illustrating an A2-A2 cross section in FIG. 27 (corresponding to FIG. 1), and FIG. 27 is a view illustrating a D2-D2 cross section in FIG. 26 (corresponding to FIG. 2).

Further, FIG. 28 is a schematic cross-sectional view of another example of the adhering substance collecting device according to the ninth embodiment. FIG. 29 is a view illustrating a positional relationship between an ejection opening and a recovery opening when the adhering substance collecting device illustrated in FIG. 28 is seen from the top. FIG. 28 is a view illustrating an A3-A3 cross section in FIG. 29 (corresponding to FIG. 1), and FIG. 29 is a view illustrating a D3-D3 cross section in FIG. 28 (corresponding to FIG. 2).

In FIG. 26 to FIG. 29, the authentication device 7 (see FIG. 1) is not illustrated.

FIG. 26 and FIG. 28 each illustrate a state in which the inspection object C is being inserted.

Here, differently from the first embodiment, adhering substance collecting devices z16 (see FIG. 26), z17 (see FIG. 28) illustrated in the ninth embodiment, the insertion opening 6 and respective recovery openings 1b, 1c are not situated at a face-to face position. That is, in the ninth embodiment, the recovery openings 1b, 1c are present on the same surface as ejection openings nF, nG, respectively.

That is, the adhering substance collecting device z16 illustrated in FIG. 26 and FIG. 27 is provided with the recovery openings 1b on central upper and lower surfaces of the housing B16. An ejection opening nF is installed to face the recovery opening 1b. As illustrated in FIG. 27, in the adhering substance collecting device z16, three pairs of the recovery openings 1b and the ejection openings nF are provided on respective three stages in a vertical direction with respect to the plane of the figure, but are not limited to the configuration.

The adhering substance collecting device z17 illustrated in FIG. 28 and FIG. 29 is provided with a pair of ejection openings nG on central upper and lower surfaces of the housing B17, respectively. With respect to the ejection openings nG, the recovery opening 1c is provided such that the ejection opening nG is interposed between a side of the insertion opening 6 and an opposite side of the insertion opening 6. As illustrated in FIG. 29, in the adhering substance collecting device z17, three pairs of the recovery openings 1c and the ejection openings nG are provided on respective three stages in an upper-lower direction with respect to the plane of the figure, but are not limited to the configuration.

Also in the present embodiment, the supporting portions H16, H17 that stabilize a positional relationship between the inspection object C and each of the ejection openings nF, nG are present, similarly to the first embodiment. Two rib-shaped portions constituting the supporting portions H16, H17 are different from those in the first embodiment and are disposed parallel to each other, but may be configured to incline toward the front side or toward the back side. Same as the first embodiment, the pipe 34 (see FIG. 26 and FIG. 28) connected to each of the recovery openings 1b, 1c is connected to the adhering substance concentration device 19.

For the shape of the supporting portions H16, H17 and the ejection openings nF, nG, the shapes illustrated in the fourth to sixth embodiments are applicable.

As illustrated in FIG. 4 and FIG. 11, the compressor 17, the pressure controller 15, the pulse valve 13, the air blower 28, and the like are connected to the pipe 34 connected to each of the ejection openings nF, nG.

In the adhering substance collecting device z16 illustrated in FIG. 26 and FIG. 27, airflow is injected toward the recovery opening 1b installed in a central part of the adhering substance collecting device z16. As a result, the adhering substances gather to the recovery opening 1b, and since the gathered adhering substances are collected from the recovery opening 1b, the collection efficiency of the adhering substances can be improved.

Further, in the adhering substance collecting device z17 illustrated in FIG. 28 and FIG. 29, since the recovery opening 1c is installed on the back side and the front side of the adhering substance collecting device z17, it is possible to prevent the adhering substances from coming out from the insertion opening 6.

Although the ejection openings nF and the recovery openings 1b are arranged in a horizontal direction in FIG. 26 and FIG. 27, the ejection openings nF may be arranged radially with respect to the recovery openings 1b.

In the same way, although the ejection openings nG and the recovery openings 1c are arranged in a horizontal direction in FIG. 28 and FIG. 29, the recovery openings 1c may be arranged radially around the ejection openings nG.

In the ninth embodiment, a positional relationship of the ejection openings nF, nG and the recovery openings 1b, 1c is not limited as long as the ejection openings nF, nG and the recovery openings 1b, 1c are present on the same surface. Inclination of the ejection opening nF in the horizontal direction in FIG. 26 is not limited, but is generally about 15° to 90° (90° is perpendicular to the inspection object C). Although not illustrated in FIG. 26 to FIG. 29, the authentication device 7 may be attached same as the first embodiment.

Tenth Embodiment

FIG. 30 is a view illustrating a positional relationship between the recovery opening, the ejection opening, and the supporting portion when the adhering substance collecting device according to the tenth embodiment is viewed from above. FIG. 31 is a schematic cross-sectional view of the adhering substance collecting device (see FIG. 30) according to the tenth embodiment. FIG. 30 illustrates an A4-A4 cross section in FIG. 31 (a figure corresponding to FIG. 2), and FIG. 31 illustrates an E4-E4 cross section in FIG. 30. In FIG. 30, the same reference numerals are given to components same as those in FIG. 2, and descriptions thereof are omitted. In FIG. 31, the same reference numerals are given to components same as those in FIG. 3, and descriptions thereof are omitted.

In addition, FIG. 30 and FIG. 31 each illustrate a state in which the inspection object C is being inserted.

A positional relationship between the ejection openings n and the recovery opening 1 in the adhering substance collecting device z18 according to the tenth embodiment is same as that of the first embodiment.

However, in a housing B18 in the adhering substance collecting device z18 according to the tenth embodiment, the insertion opening 6a is configured such that the inspection object C is inserted from a horizontal direction with respect to the recovery opening 1. It is same as the first embodiment in that the supporting portions H16, H17 for stabilizing a positional relationship between the inspection object C and the ejection openings nF, nG are present.

In the adhering substance collecting device z18 according to the tenth embodiment, since the inspection object C is inserted from the horizontal direction of the adhering substance collecting device z18, for example, when an inspection subject is standing facing the adhering substance collecting device z18, the inspection subject can easily insert the inspection object C.

For shapes of the ejection openings n and the supporting portions H, the shapes in the fourth to sixth embodiments are applicable.

Eleventh Embodiment

Next, an eleventh embodiment of the invention will be described with reference to FIG. 32 to FIG. 40.

FIG. 32 is a schematic cross-sectional view of an adhering substance collecting device according to the eleventh embodiment. FIG. 33 is a top view of the adhering substance collecting device (see FIG. 32) according to the eleventh embodiment (a drawing corresponding to FIG. 2). FIG. 34 is a schematic cross-sectional view of the adhering substance collecting device (see FIG. 32) according to the eleventh embodiment.

FIG. 32 illustrates an A5-A5 cross section in FIG. 33 (a drawing corresponding to FIG. 1), and FIG. 34 illustrates an E5-E5 cross section in FIG. 33 (a drawing corresponding to FIG. 31). In FIG. 32 to FIG. 40, the same reference numerals are given to components same as those in FIG. 1 to FIG. 3, and descriptions thereof are omitted where appropriate.

In the eleventh embodiment, same as the first embodiment, the ejection openings n incline toward the recovery opening 1 when viewed from a side cross section, and incline toward the recovery opening 1 even in a plan view. In the adhering substance collecting device z19 according to the eleventh embodiment, unlike the first to tenth embodiments, the ejection openings n are disposed only at the lower portion, and the housing B19 is configured such that an upper surface of the adhering substance collecting device z19 can be opened. Then, the inspection object C is set in the adhering substance collecting device z19, and thus, a closed space surrounded by the inspection object C and the housing B19 can be formed. In this closed space, the airflow is injected from the ejection openings n, and the adhering substances adhering to the lower surface of the inspection object C are thereby detached and collected from the recovery opening 1.

The supporting portion H having a rib shape on a surface where the ejection openings n are present is arranged same as the first embodiment, and a distance between the ejection opening n and the inspection object C is stabilized. Further, as illustrated in FIG. 32 and FIG. 33, the adhering substance collecting device z19 has a configuration in which the recovery opening 1 is arranged in front of the supporting portion H in a longitudinal direction. Reference numeral 35 denotes a distance sensor.

In the adhering substance collecting device z19 illustrated in FIG. 32 to FIG. 34, it is preferable that airflow is injected in a state where the inspection object C is manually pressed from the above.

According to the adhering substance collecting device z19 according to the eleventh embodiment, since the upper portion is configured to be openable, the inspection subject easily set the inspection object C to the adhering substance collecting device z19.

For the shape of the supporting portions H and the ejection openings n, the shapes illustrated in the fourth to sixth embodiments are applicable.

FIG. 35 is a schematic cross-sectional view illustrating another example of the adhering substance collecting device according to the eleventh embodiment. FIG. 35 is a figure corresponding to an E5-E5 cross section in FIG. 33 (a figure corresponding to FIG. 1 and FIG. 32).

Further, not only the supporting portion H is installed on a surface where the ejection openings n are arranged, the distance between the inspection object C and the ejection opening n may be stabilized in the housing B20 by using a mesh as the supporting portion H20 as in the adhering substance collecting device z20 illustrated in FIG. 35.

By doing in this way, in addition to the effect of the adhering substance collecting device z19 illustrated in FIG. 32 to FIG. 34, it is possible to increase an area where airflow hits the inspection object C, thereby improving the collection efficiency of adhering substances.

FIG. 36 is a top view of a still another example of the adhering substance collecting device according to the eleventh embodiment (a figure corresponding to FIG. 2 and FIG. 33).

A shape of the ejection opening n (see FIG. 32 to FIG. 34) is not only limited to a round shape, and is not limited to a shape such as an ellipse, such as an ejection opening nH having a slit shape like the housing B21 in the adhering substance collecting device z21 illustrated in FIG. 36. For the shape of the ejection openings n (see FIG. 32 to FIG. 34), respective shapes illustrated in the fifth embodiment are applicable. The number and position of the ejection openings n are not limited.

In addition, for the shape of the supporting portion H (see FIG. 32 to FIG. 34), respective shapes illustrated in the fourth embodiment and the sixth embodiment are applicable.

By doing in this way, in addition to the effect of the adhering substance collecting device z19 illustrated in FIG. 32 to FIG. 34, it is possible to have the effect of the adhering substance collecting devices z2 to z5, z10 to z13, and the like according to the fourth embodiment and the sixth embodiment.

FIG. 37 is a schematic cross-sectional view of the still another example of the adhering substance collecting device according to the eleventh embodiment (a figure corresponding to FIG. 1 and FIG. 32), and FIG. 38 is a top view of the adhering substance collecting device illustrated in FIG. 37 (a figure corresponding to FIG. 2 and FIG. 33).

Further, FIG. 39 is a schematic cross-sectional view of a yet another example of the adhering substance collecting device according to the eleventh embodiment, and FIG. 40 is a top view of the adhering substance collecting device illustrated in FIG. 39.

FIG. 37 illustrates an A7-A7 cross section in FIG. 38, and FIG. 39 illustrates an A8-A8 cross section in FIG. 40.

Further, in the eleventh embodiment, as illustrated in FIG. 37 to FIG. 40, the recovery openings 1d, 1e may be installed on a surface where ejection openings nI, nJ are arranged. In FIG. 37 to FIG. 40, the authentication device 7 (see FIG. 1) is not illustrated.

That is, FIG. 37 is a schematic cross-sectional view of the still another adhering substance collecting device according to the eleventh embodiment, and FIG. 38 is a view illustrating a positional relationship between the ejection opening, the supporting portion, and the recovery opening when the adhering substance collecting device illustrated in FIG. 37 is viewed from the above.

Further, FIG. 39 is a schematic cross-sectional view of the yet another adhering substance collecting device according to the eleventh embodiment, and FIG. 40 is a view illustrating a positional relationship between the ejection opening, the supporting portion, and the recovery opening when the adhering substance collecting device illustrated in FIG. 39 is viewed from the above.

Here, a difference between the adhering substance collecting device z22 in FIG. 37 and FIG. 38 and the adhering substance collecting device z23 in FIG. 39 and FIG. 40 is a difference in the positional relationship between the ejection openings nI, nJ and the recovery openings 1d, 1e.

That is, in a housing B22 of the adhering substance collecting device z22 illustrated in FIG. 37 and FIG. 38, the ejection openings nI are installed outside the recovery opening 1d. In a housing B23 of the adhering substance collecting device z23 illustrated in FIG. 39 and FIG. 40, a recovery opening 1e is installed outside the ejection opening nJ. This can also be considered as another form of the adhering substance collecting devices z16, z17 illustrated in FIG. 26 to FIG. 29 in the ninth embodiment.

The number of the ejection openings nI, nJ and the recovery openings 1d, 1e is not limited to the number illustrated in FIG. 37 to FIG. 40. Although not illustrated in FIG. 37 to FIG. 40, a coarse mesh filter 2 (see FIG. 1) may be installed on the recovery openings 1d, 1e.

As illustrated in FIG. 38, in the adhering substance collecting device z22, the ejection openings nI and the recovery openings 1d are arranged in the horizontal direction, but the ejection openings nI may be arranged radially with respect to the recovery openings 1d around the recovery openings 1d.

In the same way, as illustrated in FIG. 40, in the adhering substance collecting device z23, the ejection openings nJ and the recovery openings 1e are arranged in the horizontal direction, but the recovery openings 1e may be arranged radially around the ejection openings nJ.

In the eleventh embodiment, a positional relationship between the ejection openings nI, nJ and the recovery openings 1d, 1e are not limited as long as the ejection openings nI, nJ and the recovery openings 1d, 1e are present on the same surface. Inclination of the ejection openings nI, nJ and the recovery openings 1d, 1e in FIG. 37 to FIG. 40 is not limited, but is preferably about 15° to 90° in general (90° is perpendicular to the inspection object C). Although not illustrated in FIG. 37 to FIG. 40, the authentication device 7 may be attached same as the first embodiment.

Further, as illustrated in FIG. 38, three pairs of the ejection openings nI and the recovery openings 1d are provided in respective three stages in the vertical direction with respect to the plane of the figure, but are not limited thereto.

In the same way, as illustrated in FIG. 40, three pairs of the ejection openings nJ and the recovery openings 1e are provided in respective three stages in the vertical direction with respect to the plane of the figure, but are not limited thereto.

Further, as illustrated in FIG. 38, the supporting portion H22 is installed to be horizontal with respect to a left-right direction with respect to the plane of the figure, but shapes of the supporting portions H, H2 to H5, and H11 to H13 in the first embodiment, the fourth embodiment, and the sixth embodiment are applicable.

In the same way, as illustrated in FIG. 40, the supporting portion H23 is installed to be horizontal with respect to a left-right direction with respect to the plane of the figure, but shapes of the supporting portions H, H2 to H5, and H11 to H13 in the first embodiment, the fourth embodiment, and the sixth embodiment are applicable.

According to the adhering substance collecting device z22 illustrated in FIG. 37 and FIG. 38, in addition to the effect of the adhering substance collecting device z19 illustrated in FIG. 32 to FIG. 34, it is possible to have the effect of the adhering substance collecting device z16 (see FIG. 26 and FIG. 27) according to the ninth embodiment.

In the same way, according to the adhering substance collecting device z23 illustrated in FIG. 39 and FIG. 40, in addition to the effect of the adhering substance collecting device z19 illustrated in FIG. 32 to FIG. 34, it is possible to have the effect of the adhering substance collecting device z17 (see FIG. 28 and FIG. 29) according to the ninth embodiment.

Twelfth Embodiment

Next, a twelfth embodiment of the invention will be described with reference to FIG. 41 to FIG. 43.

FIG. 41 is a schematic cross-sectional view of an adhering substance collecting device according to the twelfth embodiment. FIG. 42 is a top view of the adhering substance collecting device (see FIG. 41) according to the twelfth embodiment (a drawing corresponding to FIG. 2 and FIG. 33). FIG. 43 is a schematic cross-sectional view of the adhering substance collecting device (see FIG. 41) according to the twelfth embodiment. In FIG. 41 to FIG. 43, the same reference numerals are given to components same as those in FIG. 1 to FIG. 3 respectively, and descriptions thereof are omitted where appropriate.

FIG. 41 illustrates an A9-A9 cross section in FIG. 42 (a figure corresponding to FIG. 1 and FIG. 32), and FIG. 43 illustrates an E9-E9 cross section in FIG. 42 (a figure corresponding to FIG. 31).

In an adhering substance collecting device z24 illustrated in FIG. 41 to FIG. 43, a protective cover 37 is attached to a housing B24 such that airflow injected from the ejection openings n does not hit an inspection subject with respect to a configuration illustrated in FIG. 32 to FIG. 34. When airflow is injected in absence of an inspection object C, the airflow is discharged to the outside of the adhering substance collecting device z24. That is, the protective cover 37 is installed such that an injection direction of the airflow is controlled. For example, there is a possibility that, when an inspection subject holds a hand over the adhering substance collecting device z24, a distance sensor 35 disadvantageously detects the hand. As a result, there is a possibility that airflow is injected in absence of the inspection object C.

In this way, when airflow is injected in presence of the inspection subject, it is not preferable in a case where a person is present in a direction of the airflow. As illustrated in FIG. 41 and FIG. 42, in the adhering substance collecting device z24, the protective cover 37 is arranged at a position where the ejection openings n face each other. That is, an extension line in a direction of the ejection openings n is designed to fit within the protective cover 37. As illustrated in FIG. 43, although usability is high as the protective cover 37 has no side wall, there may be a side wall. The height of the protective cover 37 is sufficient when a hand is easily put in, and is about 200 mm to 300 mm. Raw material of the protective cover 37 is preferably transparent.

In this way, according to the adhering substance collecting device z24 according to the twelfth embodiment, it is possible to prevent airflow from hitting the inspection subject and the like.

Thirteenth Embodiment

Next, a thirteenth embodiment of the present invention will be described with reference to FIG. 44. In FIG. 44, the same reference numerals are given to components same as those in FIG. 1, and descriptions thereof are omitted where appropriate.

FIG. 44 is a schematic cross-sectional view of an adhering substance collecting device according to the thirteenth embodiment. FIG. 44 is a cross-sectional view corresponding to an A5-A5 cross section in FIG. 33 (a figure corresponding to FIG. 1 and FIG. 32).

In a housing B25 in an adhering substance collecting device z25 illustrated in FIG. 44, the height of the supporting portion H25 is equal to or lower than the height of the recovery opening 1. By doing in this way, since airflow ejected from the ejection openings n collides on the surface of the inspection object C and then flows efficiently to the recovery opening 1, the collection efficiency is increased. That is, as illustrated in FIG. 32, when the supporting portion H is higher than the recovery opening 1, airflow toward the recovery opening 1 is generated after colliding with the housing B19 (see FIG. 32) on a side of the recovery opening 1. In such a state, collection efficiency of the adhering substances decreases. According to the thirteenth embodiment, since the airflow collides with the inspection object C, and then can flow toward the recovery opening 1 without colliding with the housing B25 on the side of the recovery opening 1, the collection efficiency can be improved.

In the first to thirteenth embodiments described so far, a length from the insertion opening 6 to the coarse mesh filter 2 is smaller than the width of the insertion opening 6. That is, the inspection object C is configured to be inserted in the transverse direction (excluding the tenth embodiment).

The present embodiment is not limited to this relationship, and the width of the insertion opening 6 may be smaller. That is, an adhering substance generation device z may be configured such that the inspection object is inserted in the longitudinal direction.

In the second embodiment, the fourth to thirteenth embodiments, an airflow apply source system Y1 is a system using the system illustrated in FIG. 4, but an airflow apply source system Y2 illustrated in FIG. 11 may be used.

The present invention is not limited to the above-described embodiments, and includes various modifications. For example, the above-described embodiments have been described in detail for easy understanding and description of the present invention, and are not necessarily limited to those having all the described configurations. Apart of a configuration of one embodiment can be replaced with a configuration of another embodiment, and the configuration of another embodiment can also be added to the configuration of one embodiment. Apart of a configuration of each embodiment can be added, deleted, or replaced with another configuration.

For example, the supporting portion H may include the supporting portion H illustrated in the first embodiment, the supporting portions H2 to H5 illustrated in the fourth embodiment, and the like.

In any of the embodiments, material of the housing B and the supporting portion H is not limited. Metal or resin may be used. In addition, a magnetic body may also be used.

The supporting portion H is not limited to a rib shape or a hemispherical shape, and may be configured such that the inspection object C can be placed, for example, hung from the upper surface of the internal space of the housing B.

Configurations, functions, and the like of the devices 25 to 26 and 40 described above may be realized with a software since a processor such as a CPU interprets and executes a program that realizes respective functions. Information such as a program, a table, a file, and the like that realizes each function can be stored in a recording device such as a memory and a solid state drive (SSD), or a recording medium such as an integrated circuit (IC) card, a secure digital (SD) card, or a digital versatile disc (DVD) in addition to being stored in a hard disk (HD).

In addition, in each embodiment, control lines and information lines illustrate those considered to be necessary on description, and not all the control lines and information lines are necessarily illustrated on the product. In practice, almost all configurations may be considered to be connected to each other.

REFERENCE SIGN LIST 1, 1a recovery opening
2 coarse mesh filter
5 infrared sensor
5a infrared sensor light emitter
5b infrared sensor light receiver
6, 6a insertion opening
7 authentication device
13 pulse valve
15 pressure controller
17 compressor
18 human sensor
19 adhering substance concentration device
20 cyclone capturing unit
22 heater
23 primary filter
24 secondary filter
25 control/data processing device
26 result display device
27 gate
28 air blower
32 shutter 35 distance sensor
40 analysis device
B, B11, B15 to B25 housing
C inspection object (object)
H, H2 to H5, H11 to H13, H15 to H17, H22, H23, H25 supporting portion (spacer)
N, nA to nJ ejection opening
Y, Y1 airflow apply source system
w inspection system
z, z1 to z25 adhering substance collecting device (adhering substance collecting unit)

The invention claimed is:

1. An adhering substance collecting device suitable to be used by inserting a card-shaped object therein, comprising:
a surface equipped with a plurality of ejection openings each of which is configured to eject gas toward a recovery opening; and
a plurality of spacers each having a protruding structure configured to:
separate a card-shaped object apart from the surface at a predetermined height from the surface, and
position the card-shaped object such that the card-shaped object separates a space surrounded by the plurality of spacers and the surface from a space above a top surface of the plurality of spacers, wherein
the recovery opening is configured to recover the gas ejected toward the card-shaped object; and
the adhering substance collecting device is configured to collect adhering substances adhering to the card-shaped object from the gas, wherein
the protruding structure of the plurality of spacers extends in a longitudinal direction from an insertion opening of the card-shaped object to the recovery opening.

2. The adhering substance collecting device according to claim 1, wherein
the surface comprises an upper surface and an opposite lower surface provided in an internal space of a housing,
the internal space accommodates the card-shaped object,
each of the plurality of spacers are disposed on the upper surface or the lower surface of the internal space, and
each spacer of the plurality of spacers has a paired spacer provided on the opposite surface.

3. The adhering substance collecting device according to claim 1, wherein each of the plurality of spacers:
has a cuboid shape,
has a paired spacer, and
is installed such that a distance between each spacer of the plurality of spacers and the paired spacer becomes smaller toward a direction of the recovery opening.

4. The adhering substance collecting device according to claim 1, wherein
a height of each spacer of the plurality of spacers is in a potential core region of the gas ejected from the ejection opening.

5. The adhering substance collecting device according to claim 1, wherein
each spacer of the plurality of spacers has a mesh structure.

6. The adhering substance collecting device according to claim 1, wherein
each spacer of the plurality of spacers are disposed in a recessed portion provided on a side surface inside a housing.

7. The adhering substance collecting device according to claim 1, wherein
in the housing, a shutter is provided in an insertion opening, and
the shutter closes when the card-shaped object is inserted into the housing.

8. The adhering substance collecting device according to claim 1, wherein the plurality of ejection openings are divided into groups, and the plurality of ejection openings are configured to eject gas at different timings for each of the groups.

9. The adhering substance collecting device according to claim 1, wherein
the surface is an opened upper surface of a housing.

10. The adhering substance collecting device according to claim 9, wherein
a protective cover is provided at least in a direction of the ejection opening on the upper surface of the housing.

11. The adhering substance collecting device according to claim 1, wherein
the ejection opening has a slit shape.

12. An inspection system comprising:
the adhering substance collecting device according to claim 1; and
an analysis unit configured to analyze the adhering substances detached by the adhering substance collecting device.

13. The inspection system according to claim 12, further comprising:
a concentration unit configured to concentrate the adhering substances detached by the adhering substance collecting device.

14. The inspection system according to claim 13, further comprising:
a cyclone capturing unit configured to concentrate adhering substances of interest by sorting out the adhering substances by centrifugal force.

* * * * *